(12) United States Patent
Baker et al.

(10) Patent No.: US 12,064,453 B2
(45) Date of Patent: Aug. 20, 2024

(54) BIOCHEMICAL AND BIOMECHANICAL CONDITIONING FOR ENHANCING PERSONALIZED MESENCHYMAL STEM CELL THERAPIES

(71) Applicant: BOARD OF REGENTS, THE UNIVERSITY OF TEXAS SYSTEM, Austin, TX (US)

(72) Inventors: Aaron B. Baker, Austin, TX (US); Jason Lee, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 69 days.

(21) Appl. No.: 16/650,195

(22) PCT Filed: Sep. 26, 2018

(86) PCT No.: PCT/US2018/052802
§ 371 (c)(1),
(2) Date: Mar. 24, 2020

(87) PCT Pub. No.: WO2019/067506
PCT Pub. Date: Apr. 4, 2019

(65) Prior Publication Data
US 2020/0268801 A1 Aug. 27, 2020

Related U.S. Application Data

(60) Provisional application No. 62/563,480, filed on Sep. 26, 2017.

(51) Int. Cl.
| | | |
|---|---|---|
| A61K 35/28 | (2015.01) | |
| A61K 9/00 | (2006.01) | |
| A61P 9/10 | (2006.01) | |
| C12N 5/071 | (2010.01) | |
| C12N 5/0775 | (2010.01) | |
| A61K 35/12 | (2015.01) | |

(52) U.S. Cl.
CPC ............ *A61K 35/28* (2013.01); *A61K 9/0019* (2013.01); *A61K 9/0024* (2013.01); *A61P 9/10* (2018.01); *C12N 5/0668* (2013.01); *C12N 5/069* (2013.01); *A61K 2035/124* (2013.01); *C12N 2501/999* (2013.01); *C12N 2527/00* (2013.01)

(58) Field of Classification Search
None
See application file for complete search history.

(56) References Cited

U.S. PATENT DOCUMENTS

| | | | | |
|---|---|---|---|---|
| 2008/0213235 A1* | 9/2008 | Katz | .................... | A61P 9/00 424/93.21 |
| 2012/0253456 A1* | 10/2012 | Shin et al. | ................ | A61F 2/82 623/1.42 |
| 2014/0273210 A1 | 9/2014 | Baker et al. | | |
| 2017/0009204 A1 | 1/2017 | Gerecht et al. | | |

FOREIGN PATENT DOCUMENTS

| | | | | |
|---|---|---|---|---|
| WO | WO-2014145871 A1 * | 9/2014 | ............ | C12N 5/069 |
| WO | WO 2017/120543 | 7/2017 | | |

OTHER PUBLICATIONS

Cantoni et al. Occurring of in Vitro Functional Vasculogenic Pericytes from Human Circulating Early Endothelial Precursor Cell Culture. Stem Cells International. vol. 2015, Article ID 943671, p. 1-11 (Year: 2015).*
Hristov et al. Endothelial Progenitor Cells: Mobilization, Differentiation, and Homing. Arterioscler Thromb Vasc Biol. 2003;23:1185-1189 (Year: 2003).*
Klaihmon et al. Distinctive Roles of YAP and TAZ in Human Endothelial Progenitor Cells Growth and Functions. Biomedicines 2022, 10, 147. p. 1-15 (Year: 2022).*
Huang et al. MiR-92a regulates endothelial progenitor cells (EPCs) by targeting GDF11 via activate SMAD2/3/FAK/Akt/eNOS pathway. Ann Transl Med 2019;7(20):563, p. 1-19 (Year: 2019).*
Loibl et al. Direct Cell-Cell Contact between Mesenchymal Stem Cells and Endothelial Progenitor Cells Induces a Pericyte-Like Phenotype in Vitro. BioMed Research International. vol. 2014, Article ID 395781, 10 pages (Year: 2014).*
Ouardy et al. Human Umbilical Cord Blood Mesenchymal Stem Cell Differentiation to Endothelial Progenitor Cells. ISESCO Journal of Science and Technology—vol. 11, No. 19 (May 2015) (2-8) (Year: 2015).*
Kuo et al. Oscillatory Shear Stress Mediates Directional Reorganization of Actin Cytoskeleton and Alters Differentiation Propensity of Mesenchymal Stem Cells. Stem Cells 2015;33:429-442 (Year: 2015).*
Xie et al. Characterization of Nestin, a Selective Marker for Bone Marrow Derived Mesenchymal Stem Cells. Stem Cells International. vol. 2015, Article ID 762098, 9 pages (Year: 2015).*

(Continued)

*Primary Examiner* — Teresa E Knight
(74) *Attorney, Agent, or Firm* — Parker Highlander PLLC

(57) ABSTRACT

A high-throughput screening system is provided for optimizing the conditioning of patient-specific mesenchymal stem cells using a combinatorial set of biochemical factors, pharmacological inhibitors, and biomechanical forces. Also provided are generalized conditions for performing such conditioning. Cells made by these methods are also provided, in addition to cells having a mixed endothelial cell/pericyte phenotype. These cells produce angiogenic growth factors and induce vascularization following implantation.

12 Claims, 29 Drawing Sheets

(56) References Cited

OTHER PUBLICATIONS

Dong et al. Response of mesenchymal stem cells to shear stress in tissue engineered vascular grafts. Acta Pharmacol Sin May 2009; 30 (5): 530-536 (Year: 2009).*
Hansen et al. YAP and TAZ: a nexus for Hippo signaling and beyond. Trends Cell Biol. Sep. 2015 ; 25(9): 499-513 (Year: 2015).*
Rabbani et al. Effects of Uniaxial Cyclic Stretch Loading on Morphology of Adipose Derived Stem Cells. Tissue Eng Regen Med 2016;13(4):396-402 (Year: 2016).*
Ai, Wen-Jia, et al. "R-Smad signaling-mediated VEGF expression coordinately regulates endothelial cell differentiation of rat mesenchymal stem cells." *Stem cells and development* 24.11 (2015): 1320-1331.
Alaminos, Miguel, et al. "Transdifferentiation potentiality of human Wharton's jelly stem cells towards vascular endothelial cells." *Journal of cellular physiology* 223.3 (2010): 640-647.
Armulik, Annika, Guillem Genové, and Christer Betsholtz. "Pericytes: developmental, physiological, and pathological perspectives, problems, and promises." *Developmental cell* 21.2 (2011): 193-215.
Bai, Ke, et al. "Endothelium oriented differentiation of bone marrow mesenchymal stem cells under chemical and mechanical stimulations." *Journal of biomechanics* 43.6 (2010): 1176-1181.
Bailey, Brandi, et al. "Sca-1 knockout impairs myocardial and cardiac progenitor cell function." *Circulation research* 111.6 (2012): 750-760.
Baraniak, Priya R., and Todd C. McDevitt. "Stem cell paracrine actions and tissue regeneration." *Regenerative medicine* 5.1 (2010): 121-143.
Barbash, Israel M., et al. "Systemic delivery of bone marrow-derived mesenchymal stem cells to the infarcted myocardium: feasibility, cell migration, and body distribution." *Circulation* 108.7 (2003): 863-868.
Barkholt, Lisbeth, et al. "Risk of tumorigenicity in mesenchymal stromal cell-based therapies—bridging scientific observations and regulatory viewpoints." *Cytotherapy* 15.7 (2013): 753-759.
Birbrair, Alexander, et al. "Role of pericytes in skeletal muscle regeneration and fat accumulation." *Stem cells and development* 22.16 (2013): 2298-2314.
Birbrair, Alexander, et al. "Type-2 pericytes participate in normal and tumoral angiogenesis." *American Journal of Physiology-Cell Physiology* 307.1 (2014): C25-C38.
Brown, Thomas D. "Techniques for mechanical stimulation of cells in vitro: a review." *Journal of biomechanics* 33.1 (2000): 3-14.
Bussolino, Federico, et al. "Hepatocyte growth factor is a potent angiogenic factor which stimulates endothelial cell motility and growth." *The Journal of cell biology* 119.3 (1992): 629-641.
Cai, Mengting, et al. "PET monitoring angiogenesis of infarcted myocardium after treatment with vascular endothelial growth factor and bone marrow mesenchymal stem cells." *Amino Acids* 48.3 (2016): 811-820.
Cai, Min, et al. "Bone marrow mesenchymal stem cells (BM-MSCs) improve heart function in swine myocardial infarction model through paracrine effects." *Scientific reports* 6.1 (2016): 1-12.
Cassino, Theresa R., et al. "Mechanical loading of stem cells for improvement of transplantation outcome in a model of acute myocardial infarction: the role of loading history." *Tissue Engineering Part A* 18.11-12 (2012): 1101-1108.
Crisan, Mihaela, et al. "A perivascular origin for mesenchymal stem cells in multiple human organs." *Cell stem cell* 3.3 (2008): 301-313.
Deng et al., "Inhibition of Protein Kinase C $\beta_2$ Prevents Tumor Necrosis Factor-α-Induced Apoptosis and Oxidative Stress in Endothelial Cells: The Role of NADPH Oxidase Subunits." *J Vasc Res* 2012;49:144-149.
Di Bernardini, Elisabetta, et al. "Endothelial lineage differentiation from induced pluripotent stem cells is regulated by microRNA-21 and transforming growth factor β2 (TGF-β2) pathways." *Journal of Biological Chemistry* 289.6 (2014): 3383-3393.
Dong, Jian-de, et al. "Response of mesenchymal stem cells to shear stress in tissue-engineered vascular grafts." *Acta pharmacologica sinica* 30.5 (2009): 530-536.

Du, Wen Jing, et al. "Heterogeneity of proangiogenic features in mesenchymal stem cells derived from bone marrow, adipose tissue, umbilical cord, and placenta." *Stem cell research & therapy* 7.1 (2016): 1-11.
Duong-Ly, et al., "Kinase Inhibitor Profiling Reveals Unexpected Opportunities to Inhibit Disease-Associated Mutant Kinases." *Cell Reports* 14, 772-781, Feb. 2, 2016.
Engler, Adam J., et al. "Matrix elasticity directs stem cell lineage specification." *Cell* 126.4 (2006): 677-689.
Espagnolle, Nicolas, et al. "CD 146 expression on mesenchymal stem cells is associated with their vascular smooth muscle commitment." *Journal of cellular and molecular medicine* 18.1 (2014): 104-114.
Galas Jr, Richard J., and Julie C. Liu. "Vascular endothelial growth factor does not accelerate endothelial differentiation of human mesenchymal stem cells." *Journal of cellular physiology* 229.1 (2014): 90-96.
Goldie, Lauren C., Melissa K. Nix, and Karen K. Hirschi. "Embryonic vasculogenesis and hematopoietic specification." *VEGF in Development*. Springer, New York, NY, 2008. 40-51.
Heeschen, Christopher, et al. "Profoundly reduced neovascularization capacity of bone marrow mononuclear cells derived from patients with chronic ischemic heart disease." *Circulation* 109.13 (2004): 1615-1622.
Heldin, Carl-Henrik, et al. "High interstitial fluid pressure—an obstacle in cancer therapy." *Nature Reviews Cancer* 4.10 (2004): 806-813.
Henderson, et al., "Biomechanical Regulation of Mesenchymal Stem Cells for Cardiovascular Tissue Engineering." *Advanced Healthcare Materials* (2017).
Hill, et al., "Emerging roles of pericytes in the regulation of the neurovascular unit in health and disease." *J Neuroimmune Pharmacol.* Dec. 2014; 9(5):591-605.
Hill, Jonathan M., et al. "Circulating endothelial progenitor cells, vascular function, and cardiovascular risk." *New England Journal of Medicine* 348.7 (2003): 593-600.
Holmes, Christina, and William L. Stanford. "Concise review: stem cell antigen-1: expression, function, and enigma." *Stem cells* 25.6 (2007): 1339-1347.
Jain, Rakesh K., John D. Martin, and Triantafyllos Stylianopoulos. "The role of mechanical forces in tumor growth and therapy." *Annual review of biomedical engineering* 16 (2014): 321-346.
Janeczek Portalska, Karolina, et al. "Endothelial differentiation of mesenchymal stromal cells." (2012): e46842.
Kamotani, Yoko, et al. "Individually programmable cell stretching microwell arrays actuated by a Braille display." *Biomaterials* 29.17 (2008): 2646-2655.
Kim, Dong Hwa, et al. "Shear stress and circumferential stretch by pulsatile flow direct vascular endothelial lineage commitment of mesenchymal stem cells in engineered blood vessels." *Journal of Materials Science: Materials in Medicine* 27.3 (2016): 60.
Kim, et al., "YAP/TAZ regulates sprouting angiogenesis and vascular barrier maturation." *J Clin Ivest.* 2017; 127(9):3441-3461.
Kinnaird, T., et al. "Local delivery of marrow-derived stromal cells augments collateral perfusion through paracrine mechanisms." *Circulation* 109.12 (2004): 1543-1549.
Korn, Johannes, Bodo Christ, and Haymo Kurz. "Neuroectodermal origin of brain pericytes and vascular smooth muscle cells." *Journal of Comparative Neurology* 442.1 (2002): 78-88.
Kretlow, James D., et al. "Donor age and cell passage affects differentiation potential of murine bone marrow-derived stem cells." *BMC cell biology* 9.1 (2008): 1-13.
Lee, David A., et al. "Stem cell mechanobiology." *Journal of cellular biochemistry* 112.1 (2011): 1-9.
Lee, et al. "A Novel System for Studying Mechanical Strain Waveform-Dependent Responses in Vascular Smooth Muscle Cells." *Lab Chip.* Dec. 7, 2013; 13(23): 4573-4582.
Lee, Jason, and Aaron B. Baker. "Computational analysis of fluid flow within a device for applying biaxial strain to cultured cells." *Journal of biomechanical engineering* 137.5 (2015).
Li, Ning, Zeeshan Pasha, and Muhammad Ashraf. "Reversal of ischemic cardiomyopathy with Sca-1+ stem cells modified with multiple growth factors." *PloS one* 9.4 (2014): e93645.

(56) References Cited

OTHER PUBLICATIONS

Li, Ning, Zeeshan Pasha, and Muhammad Ashraf. "Correction: Reversal of Ischemic Cardiomyopathy with Sca-1+ Stem Cells Modified with Multiple Growth Factors." *PloS one* 15.2 (2020): e0229293.

Li, Qiming, et al. "VEGF treatment promotes bone marrow-derived CXCR4+ mesenchymal stromal stem cell differentiation into vessel endothelial cells." *Experimental and therapeutic medicine* 13.2 (2017): 449-454.

Li, Tao-Sheng, et al. "Impaired potency of bone marrow mononuclear cells for inducing therapeutic angiogenesis in obese diabetic rats." *American Journal of Physiology—Heart and Circulatory Physiology* 290.4 (2006): H1362-H1369.

Liu, et al., "Epidermal Growth Factor Inhibits Transforming Growth Factor-β-Induced Fibrogenic Differentiation Marker Expression through ERK Activation." *Cell Signal*, Oct. 2014; 26(10); 2276-2283.

MacQueen, Luke, Yu Sun, and Craig A. Simmons. "Mesenchymal stem cell mechanobiology and emerging experimental platforms." *Journal of the Royal Society Interface* 10.84 (2013): 20130179.

Moghadam, Farshad Homayouni, et al. "Treatment with platelet lysate induces endothelial differentiation of bone marrow mesenchymal stem cells under fluid shear stress." *EXCLI journal* 13 (2014): 638.

Müller-Ehmsen, Jochen, et al. "Effective engraftment but poor mid-term persistence of mononuclear and mesenchymal bone marrow cells in acute and chronic rat myocardial infarction." *Journal of molecular and cellular cardiology* 41.5 (2006): 876-884.

Nagaya, Noritoshi, et al. "Intravenous administration of mesenchymal stem cells improves cardiac function in rats with acute myocardial infarction through angiogenesis and myogenesis." *American Journal of Physiology—Heart and circulatory physiology* 287.6 (2004): H2670-H2676.

Oswald, Joachim, et al. "Mesenchymal stem cells can be differentiated into endothelial cells in vitro." *Stem cells* 22.3 (2004): 377-384.

PCT International Search Report and Written Opinion for PCT/US2018/052802; Jan. 16, 2019.

Phinney, D.G. "Functional heterogeneity of mesenchymal stem cells: implications for cell therapy." *J Cell Biochem* 113, 2806-2812 (2012).

Roobrouck, Valerie D., Fernando Ulloa-Montoya, and Catherine M. Verfaillie. "Self-renewal and differentiation capacity of young and aged stem cells." *Experimental cell research* 314.9 (2008): 1937-1944.

Russell, Katie C., et al. "Cell-surface expression of neuron-glial antigen 2 (NG2) and melanoma cell adhesion molecule (CD146) in heterogeneous cultures of marrow-derived mesenchymal stem cells." *Tissue engineering Part A* 19.19-20 (2013): 2253-2266.

Shake, Jay G., et al. "Mesenchymal stem cell implantation in a swine myocardial infarct model: engraftment and functional effects." *The Annals of thoracic surgery* 73.6 (2002): 1919-1926.

Shi, Yufang, et al. "Mesenchymal stem cells: a new strategy for immunosuppression and tissue repair." *Cell research* 20.5 (2010): 510-518.

Simmons, C. S., et al. "Integrated strain array for cellular mechanobiology studies." *Journal of Micromechanics and Microengineering* 21.5 (2011): 054016.

Spencer, Adrianne, et al. "A high-throughput mechanofluidic screening platform for investigating tumor cell adhesion during metastasis." *Lab on a Chip* 16.1 (2016): 142-152.

Spruell, Christopher, and Aaron B. Baker. "Analysis of a high-throughput cone-and-plate apparatus for the application of defined spatiotemporal flow to cultured cells." *Biotechnology and bioengineering* 110.6 (2013): 1782-1793.

Tamama, Kenichi, Chandan K. Sen, and Alan Wells. "Differentiation of bone marrow mesenchymal stem cells into the smooth muscle lineage by blocking ERK/MAPK signaling pathway." *Stem cells and development* 17.5 (2008): 897-908.

Tsai, Chih-Chien, and Shih-Chieh Hung. "Functional roles of pluripotency transcription factors in mesenchymal stem cells." *Cell cycle* 11.20 (2012): 3711-3712.

Voyvodic, Peter L., Daniel Min, and Aaron B. Baker. "A multi-channel dampened flow system for studies on shear stress-mediated mechanotransduction." *Lab on a Chip* 12.18 (2012): 3322-3330.

Wagner, Wolfgang, et al. "Aging and replicative senescence have related effects on human stem and progenitor cells." *PloS one* 4.6 (2009): e5846.

Wang, Hao, et al. "Shear stress induces endothelial differentiation from a murine embryonic mesenchymal progenitor cell line." *Arteriosclerosis, thrombosis, and vascular biology* 25.9 (2005): 1817-1823.

Wanjare et al., Perivascular cells in blood vessel regeneration; *Biotechnol J.* Apr. 2013; 8(4): 434-447.

Watt, Suzanne M., et al. "The angiogenic properties of mesenchymal stem/stromal cells and their therapeutic potential." *British medical bulletin* 108.1 (2013): 25-53.

Wu, Cheng-Chi, et al. "CD146+ mesenchymal stem cells display greater therapeutic potential than CD146-cells for treating collagen-induced arthritis in mice." *Stem cell research & therapy* 7.1 (2016): 1-13.

Xie, Liang, et al. "Characterization of nestin, a selective marker for bone marrow derived mesenchymal stem cells." *Stem cells international* 2015 (2015).

Yan, Jinglian, et al. "Mesenchymal stem cells as a treatment for peripheral arterial disease: current status and potential impact of type II diabetes on their therapeutic efficacy." *Stem cell reviews and reports* 9.3 (2013): 360-372.

Yang, Michael T., et al. "Assaying stem cell mechanobiology on microfabricated elastomeric substrates with geometrically modulated rigidity." *Nature protocols* 6.2 (2011): 187-213.

Zhang, et al. "Blood flow and stem cells in vascular disease." *Cardiovascular Research* (2013) 99, 251-259.

\* cited by examiner

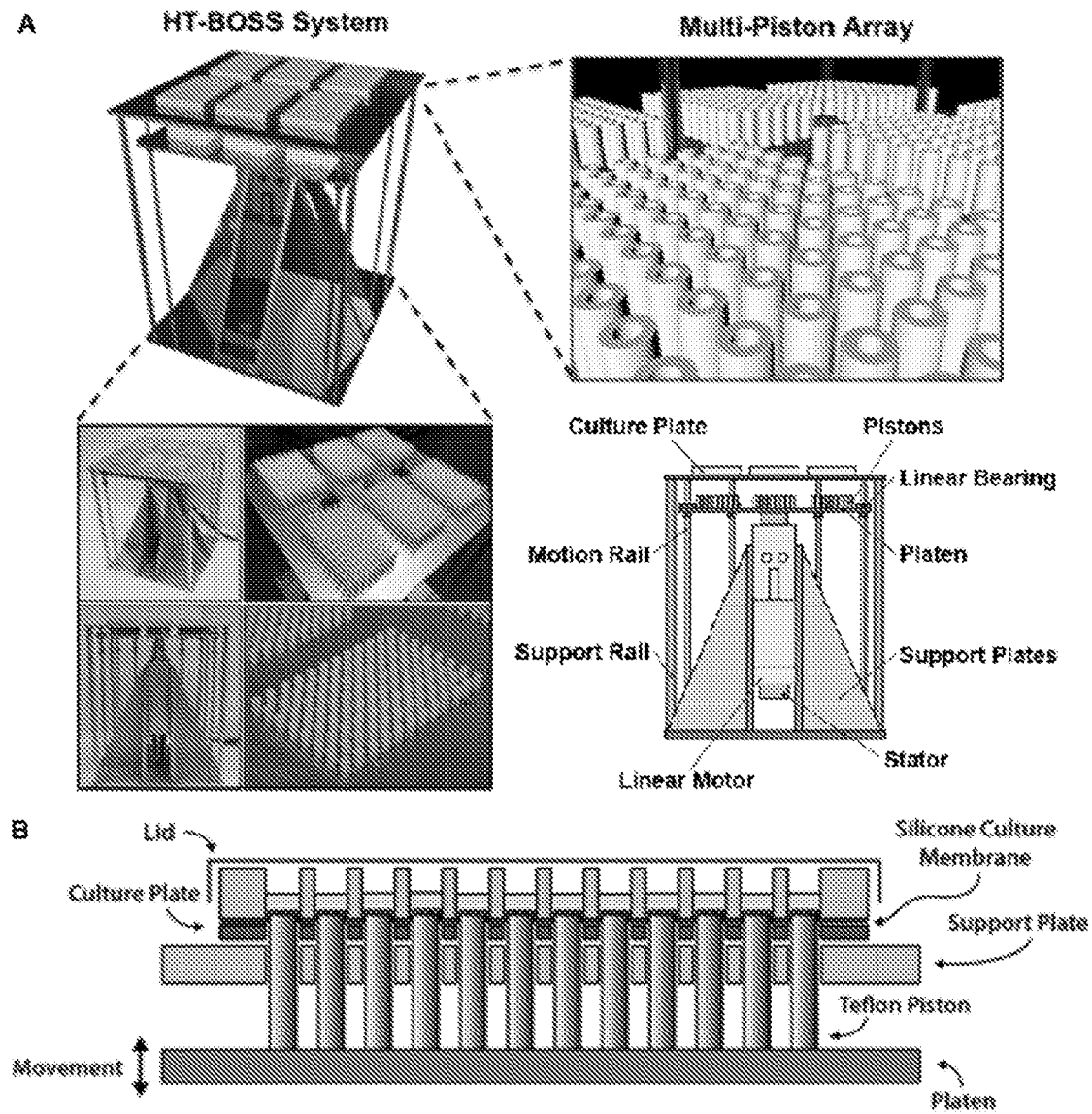
FIGS. 1A-B

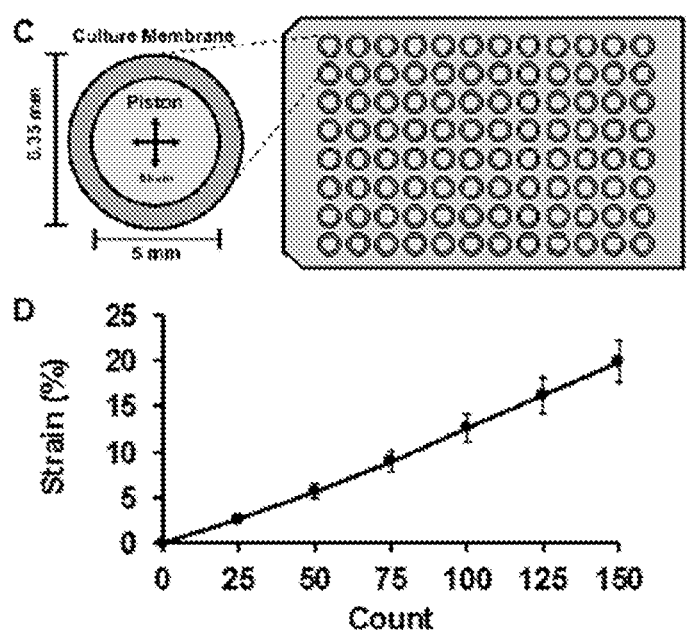
FIGS. 1C-D

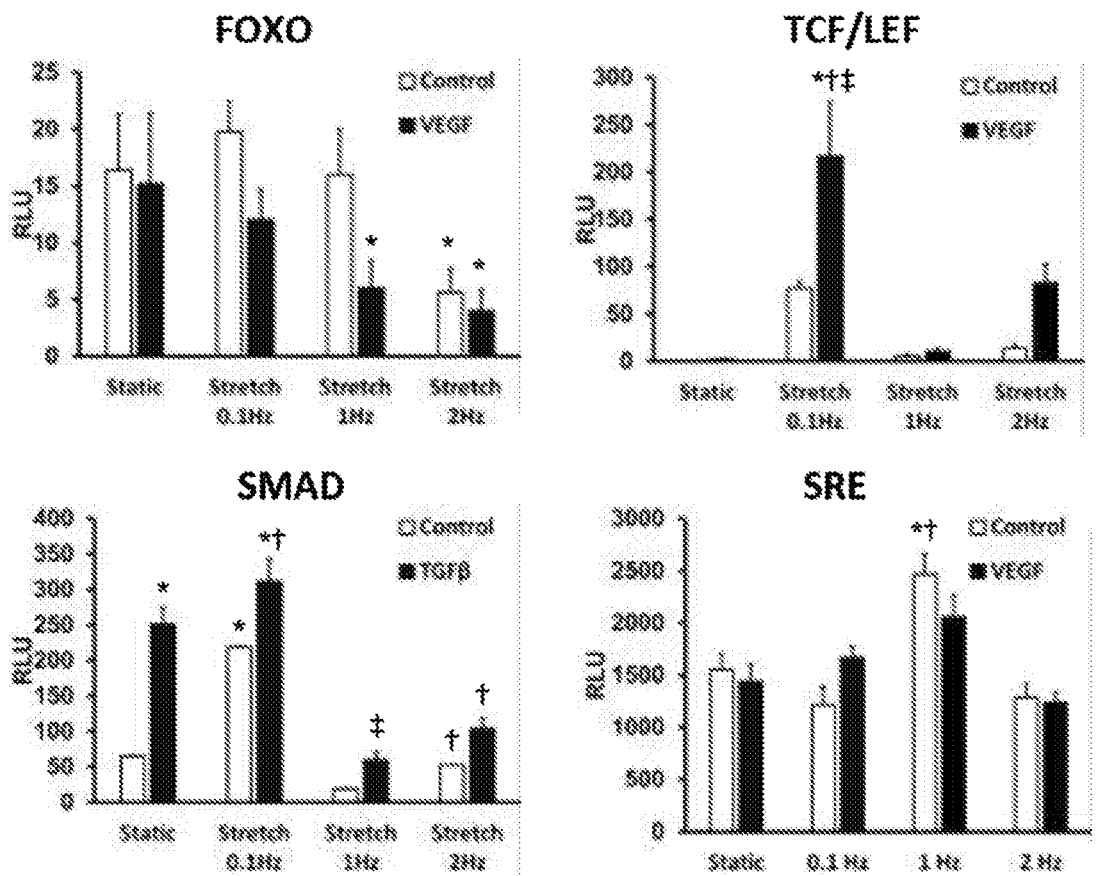
FIG. 2A
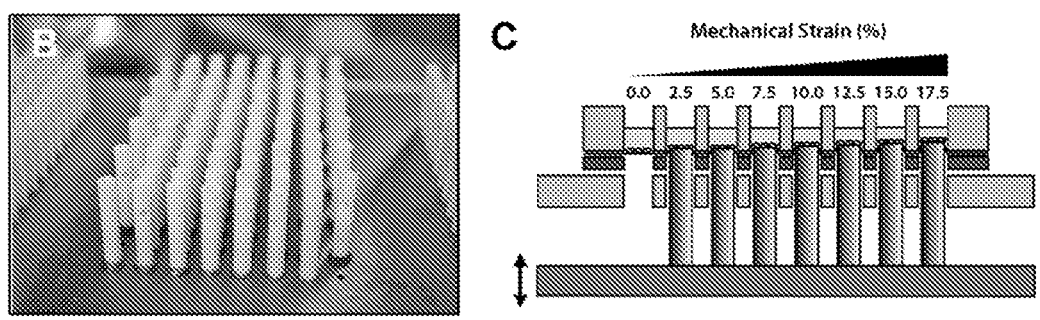
FIGS. 2B-C

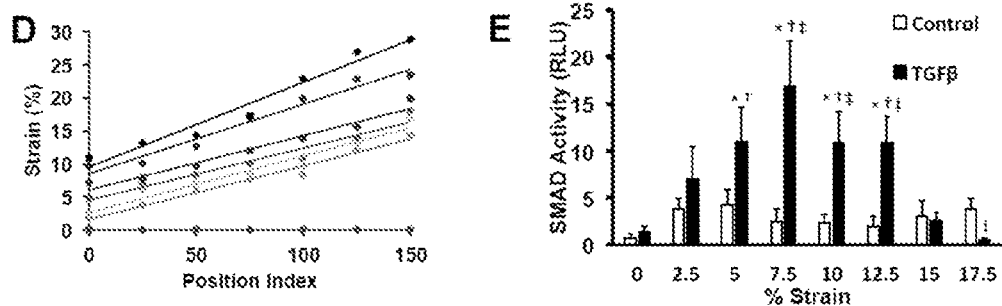
FIGS. 2D-E
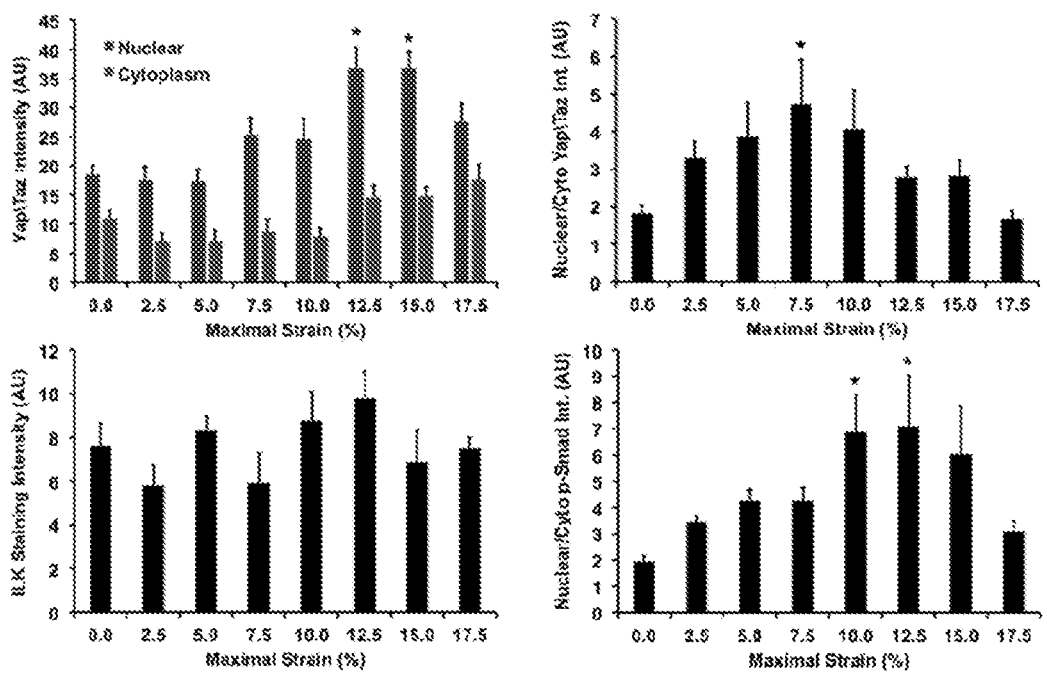
FIG. 2F

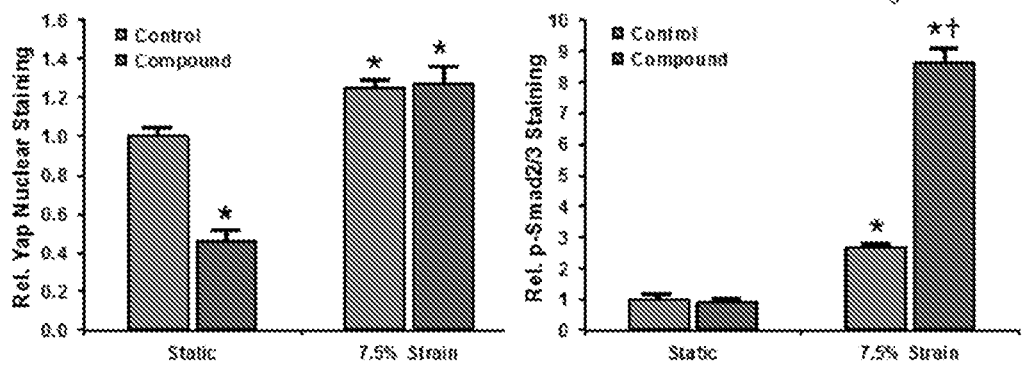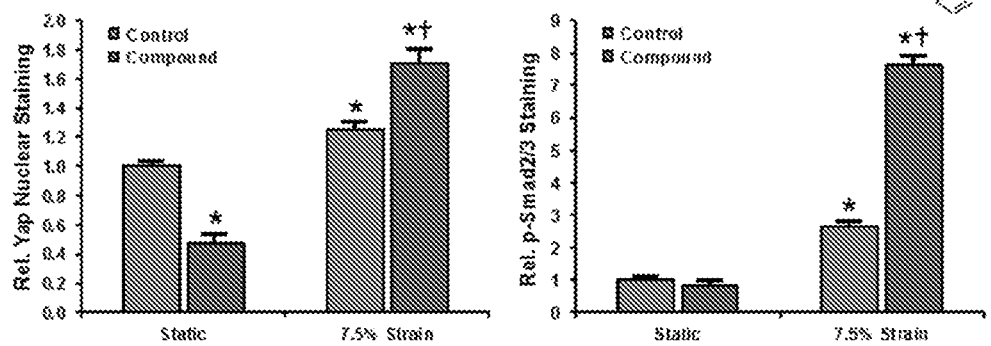
FIG. 4A

EGFR Inhibitor
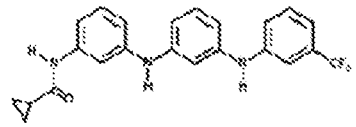
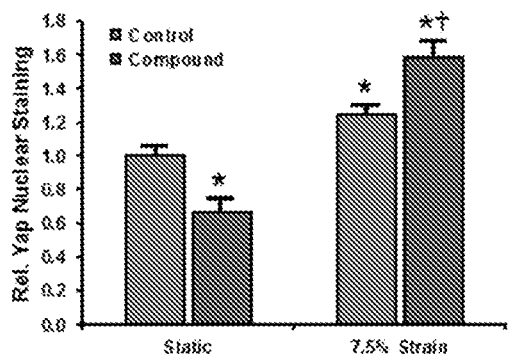
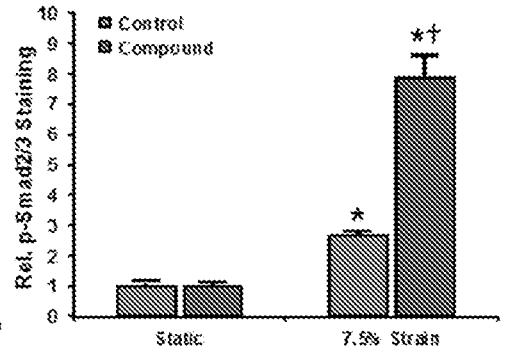
Fyn/Src Inhibitor
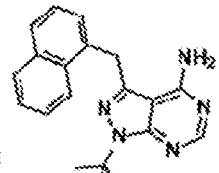
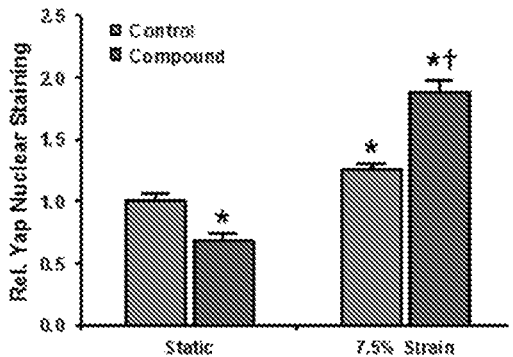
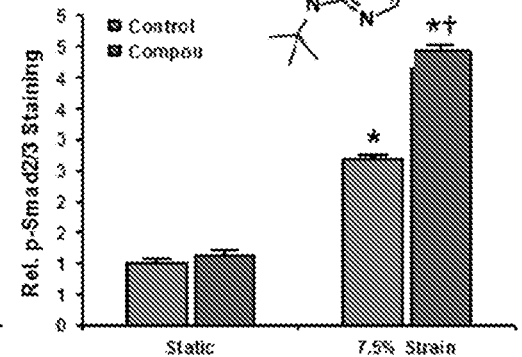
FIG. 4A (cont.)

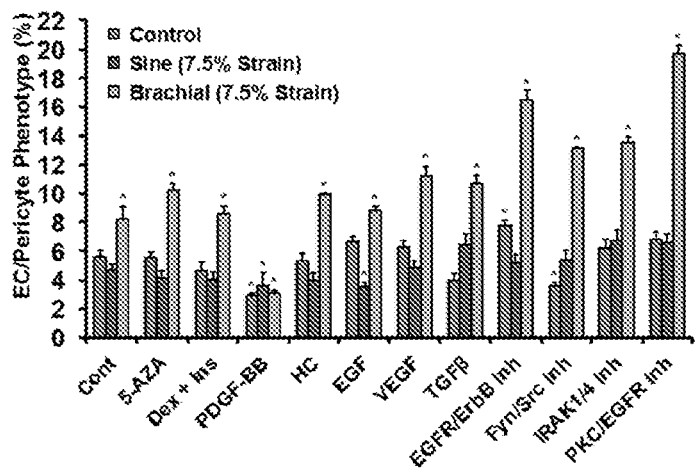
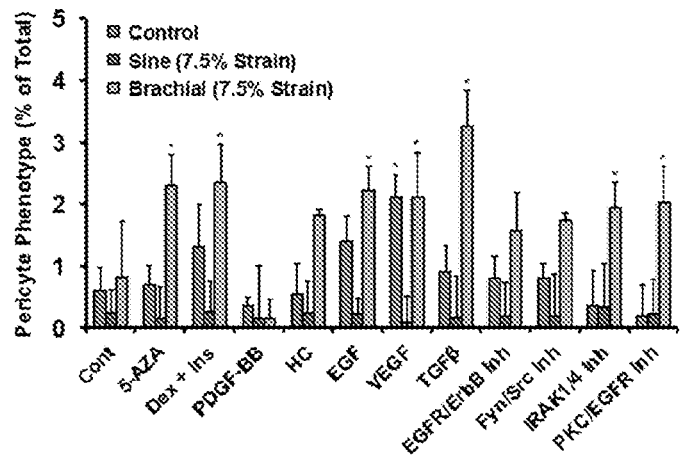
FIG. 5B (cont.)

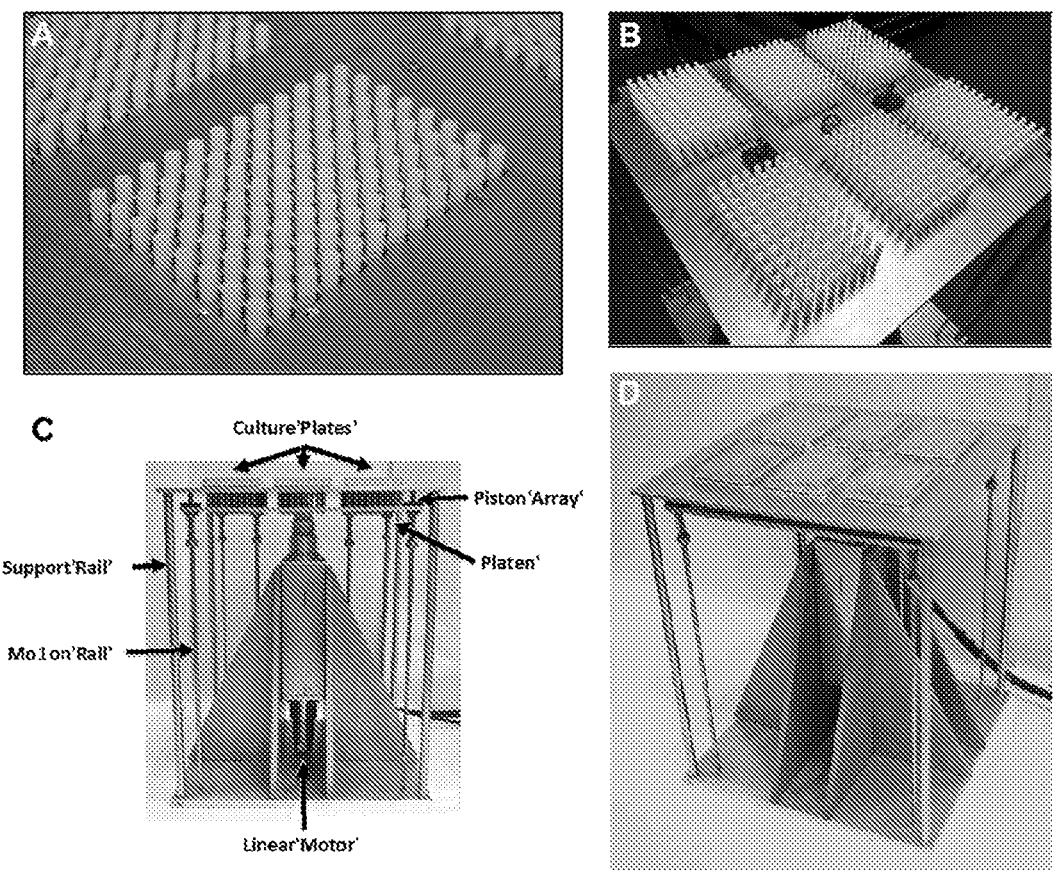
FIGS. 7A-D

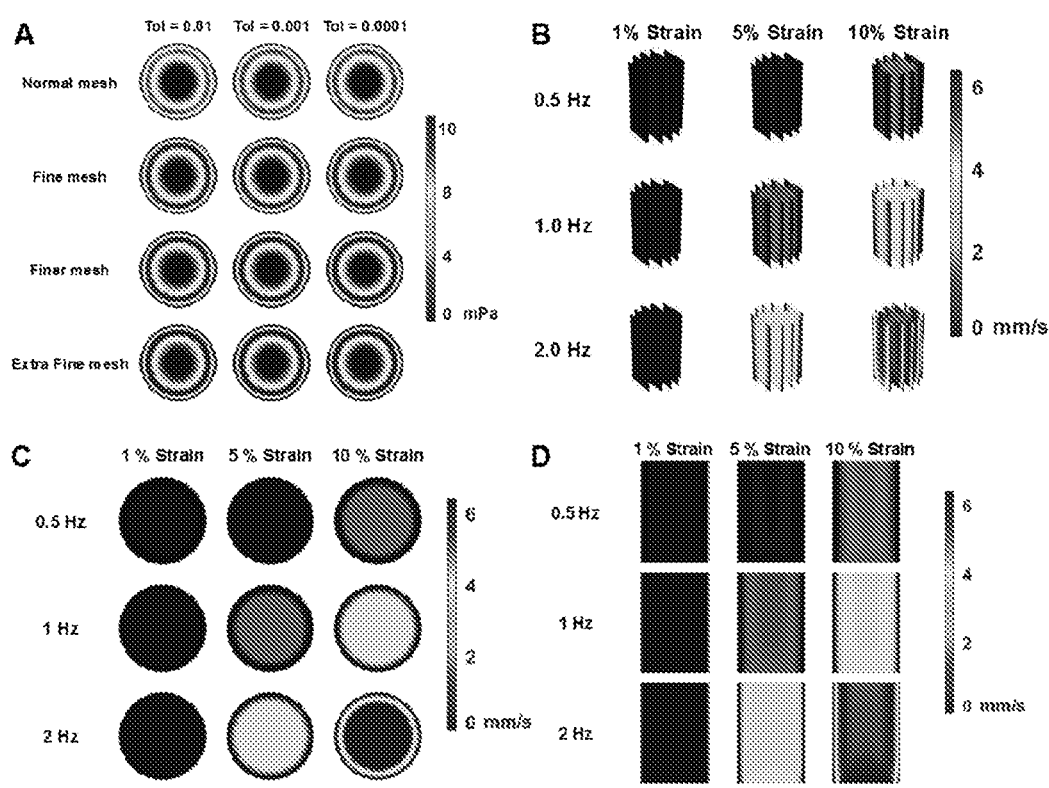
FIGS. 8A-D

BIOCHEMICAL AND BIOMECHANICAL CONDITIONING FOR ENHANCING PERSONALIZED MESENCHYMAL STEM CELL THERAPIES

The present application is a national phase application under 35 U.S.C. § 371 of International Application No. PCT/US2018/052802, filed Sep. 26, 2018, which claims the priority benefit of U.S. provisional application No. 62/563,480, filed Sep. 26, 2017, the entire contents of each of which is incorporated herein by reference.

This invention was made with government support under Grant Nos. OD008716 and R01 HL141761 awarded by the National Institutes of Health. The government has certain rights in the invention.

BACKGROUND

1. Field

The present invention relates generally to the fields of cell biology and therapeutics. More particularly, it concerns mesenchymal stem cells having a mixed endothelial/pericyte phenotype, as well as methods of producing said cells, and high-throughput methods for producing personalized mesenchymal stem cell-based therapeutics, as well as compositions produced by said methods.

2. Description of Related Art

Cell based therapies have great potential for revolutionizing the treatment of disease that are not amenable to traditional therapies. Therapies based on mesenchymal stem cells (MSCs) are particularly appealing as they are a source of autologous cells with diverse multipotency and can be harvested from patients with relative ease. In addition, MSCs are able to self-renew and have immunosuppressive properties that make them ideal candidates for autologous cellular therapeutics (Shi et al., 2010). For cardiovascular therapies, MSCs have been explored for the treatment of myocardial infarct and peripheral ischemia (Shake et al., 2002; Barbash et al., 2003; Nagaya et al., 2004; Muller-Ehmsen et al., 2006; Cai et al., 2016a; Cai et al., 2016b). However, these trials have not shown consistent long-term benefit from MSC therapies in spite of the intense investigation by many groups (Baraniak & McDevitt, 2010; Cassino et al., 2012; Watt et al., 2013; Yan et al., 2013). There are several limitations in the current application of MSCs for therapeutic use. In conventional culture, MSCs lose differentiation potential and have reduced therapeutic potential during ex vivo expansion (Wagner et al., 2009; Kretlow et al., 2008). In addition, the isolated MSC population has a high degree of heterogeneity and subsets of these cells have varying degrees of potential for inducing regeneration (Phinney, 2012; Du et al., 2016). Moreover, the therapeutic potential of MSCs is altered by the health of the patient from which they are harvested. This is a major limitation as patients with advanced age, obesity, diabetes and other chronic disorders have MSCs with altered differentiation potential and regenerative properties (Wagner et al., 2009; Kretlow et al., 2008; Heeschen et al., 2004; Hill et al., 2003; Li et al., 2006; Roobrouck et al., 2008). Genetic modification of MSCs could address some of these issues but also raise concerns of tumorigenicity (Barkholt et al., 2013). Thus, there is intense an interest in identifying alternative strategies for making MSCs more effective and reliable in the face of patient-to-patient differences in MSC behavior.

Recently, there is increasing recognition that biophysical forces are important modulators of biological processes in many fields including cancer (Jain et al., 2014; Heldin et al., 2004), stem cell biology (Lee et al., 2011; Yang et al., 2011; Engler et al., 2006), and embryological development (Goldie et al., 2008). While many fields have experienced a massive increase in the experimental throughput in the past decades driven by the development and widespread adoption of plate reader, robotic pipetting, and automated imaging systems, the available systems for studying the effects of applied mechanical forces remain limited by the low throughput and the limited ability to apply complex dynamic forces that simulate those in the body. This limitation not only slows the progress of research but also changes the nature of the studies that can be performed, leading to an incomplete exploration of the "dose response" to mechanical forces and their synergy with biochemical signals. Thus, studies of cellular mechanobiology are eminently impractical for pathway discovery and drug screening and requires experimental throughput far beyond the capability of these conventional systems.

The differentiation of MSCs into endothelial cells would be highly advantageous for many clinical applications including the treatment of ischemia and endothelialization of vascular grafts. Unfortunately, there has not been a consensus in the field as to what conditions induce endothelial differentiation in MSCs or even if the phenotype obtained is truly endothelial in nature (Oswald et al., 2004; Li et al., 2017; Laneczek Portalska et al., 2012; Galad & Liu, 2014). Mechanical forces, including shear stress and mechanical stretch, have been used to condition MSCs into vascular phenotypes (Henderson et al., 2017; Homayouni Moghadam et al., 2014; Bai et al., 2010; Dong et al., 2009; Kim et al., 2016; Wang et al., 2005). Several studies have shown that shear stress and treatments, such as VEGF, can lead to the expression of endothelial markers in MSCs (Oswald et al., 2004; Janeczek Portalska et al., 2012). However, some studies have found contrasting results, depending on the source and the specific MSC cell line and increases in markers for vascular smooth muscle cells (vSMCs) in combination with those for endothelial cells (Kim et al., 2016; Wang et al., 2005; Kinnaird et al., 2004; Alaminos et al., 2010). Thus, it is unclear what conditions are optimal for obtaining an endothelial cell-like phenotype in MSCs, and in clinical practice, it is likely that patient specific MSCs may respond differently to specific treatments.

SUMMARY

Specific conditions have been identified for treating MSCs to enhance their ability to induce angiogenesis, providing a major advantage over non-treated MSCs. In addition, the screening assay provides a general means to identify patient-specific conditions for enhancing MSC therapies to treat any type of disease. To this end, a high throughput system was developed for applying mechanical stretch to cultured cells that uses a modular multi-well plate format and is capable of accurately applying mechanical force to 576 individual culture wells simultaneously. Using a true linear motor, the system is capable of recapitulating the complex dynamic strain waveforms found in arteries and other parts of the body. Using this system, a set of screening assays was performed that explored the synergy between biochemical factors, pharmacological inhibitors, and biomechanical forces in conditioning MSCs into vascular cell-like phenotypes that have enhanced regenerative properties. These studies revealed that a specific dynamic mechanical loading waveform had a pronounced ability to enhance the expression of endothelial markers in MSCs. Moreover, several pharmacological inhibitors were identified that synergistically increase endothelial markers in combination with optimal mechanical loading conditions. A detailed analysis of the MSC phenotype of these mechanically and pharmacologically conditioned cells revealed that these cells have a mixed phenotype with increased expression of endothelial markers concomitantly expressed with markers for pericytes. This mixed phenotype has enhanced pericyte-like behavior and production of pro-angiogenic paracrine factors, and induces enhanced angiogenesis in comparison to non-conditioned cells on implantation.

In one embodiment, provided herein are cells comprising both an endothelial phenotype and a pericyte phenotype. In some aspects, the phenotype is characterized by the expression of PECAM-1, CD105, VECad, CD146, Nestin, and PDGFRβ. In some aspects, the cells are not genetically modified. In some aspects, the pericyte phenotype is a type 2 pericyte phenotype. In some aspects, the pericyte phenotype is a type 1 pericyte phenotype. In some aspects, the cells express NG2. In some aspects, the cells have increased YAP/TAZ activation and increased SMAD2/3 activation.

In one embodiment, provided herein are methods of enhancing the combined pericyte/endothelial character of mesenchymal stem cells (MSCs), the method comprising (a) obtaining a starting population of mesenchymal stem cells; (b) culturing the mesenchymal stem cells on a flexible surface that allows cell adhesion; and (c) applying a controlled shear stress/mechanical stretch to the mesenchymal stem cells with a force sufficient to produce a conditioned composition comprising cells having a combined pericyte/endothelial character.

In some aspects, the methods further comprise (d) incubating the mesenchymal stem cells with at least one pharmacological agent that inhibits EGFR signaling. In certain aspects, the agent inhibits either EGFR/ErbB signaling or EGFR/PKC signaling. In certain aspects, the agent enhances Smad2/3 and/or Hippo pathway activation. In certain aspects, the agent is a kinase inhibitor, such as, for example, an EGFR/ErB-2/4 inhibitor or a PKCβII/EGFR inhibitor.

In some aspects, the methods further comprise (d) incubating the mesenchymal stem cells with at least one biochemical agent. In some aspects, the biochemical agent is TGFβ.

In some aspects, the methods produce MSCs having enhanced angiogenic potential. In some aspects, obtaining a starting population of mesenchymal stem cells comprises harvesting mesenchymal stem cells from the bone marrow or the adipose tissue of a patient.

In some aspects, the shear stress/mechanical stretch is generated using a true linear motor. In some aspects, the shear stress/mechanical stretch is applied using a waveform. In certain aspects, the waveform is a dynamic mechanical loading waveform. In certain aspects, the dynamic mechanical loading waveform is a brachial waveform. In certain aspects, the waveform is a sine waveform. In some aspects, the dynamic mechanical loading waveform has a frequency of 0.1 Hz-1.00 Hz. In some aspects, the dynamic mechanical loading waveform has a magnitude of strain of from 0.1% to 17.5%. In certain aspects, the dynamic mechanical loading waveform has a magnitude of 7.5% strain and a frequency of 0.1 Hz.

In one embodiment, provided herein are methods for identifying conditions for enhancing mesenchymal stem cell (MSC) therapies for a patient, the method comprising (a) obtaining from the patient a starting population of mesenchymal stem cells (MSCs); (b) preparing multiple, separate cultures of the patient's MSCs on flexible surfaces that allow cell adhesion; (c) applying a variety of controlled shear stresses/mechanical stretches to each of the MSCs; and (d) screening the cultured cells for markers of a combined pericyte/endothelial cell phenotype, thereby identifying conditions for enhancing MSC therapies for the patient.

In some aspects, the methods further comprise (c1) incubating each of the cultures with at least one pharmacological agent that inhibits EGFR signaling. In certain aspects, the agent inhibits either EGFR/ErbB signaling or EGFR/PKC signaling. In certain aspects, the agent enhances Smad2/3 and/or Hippo pathway activation. In certain aspects, the agent is a kinase inhibitor. In certain aspects, the agent is an EGFR/Erb-2/4 inhibitor. In certain aspects, the agent is a PKCβII/EGFR inhibitor.

In some aspects, the methods further comprise (c1) incubating each of the cultures with at least one biochemical agent. In certain aspects, the biochemical agent is TGFβ.

In some aspects, the methods identify conditions for producing MSCs having enhanced angiogenic potential. In some aspects, the methods identify conditions that increase the regenerative capacity of the patient's MSCs.

In some aspects, obtaining a starting population of mesenchymal stem cells comprises harvesting mesenchymal stem cells from the bone marrow or adipose tissue of a patient. In some aspects, the markers of a combined pericyte/endothelial cell phenotype comprise nuclear localization of YAP/TAZ, phosphorylation of SMAD2/3, nuclear localization of SMAD2/3, and increased expression of PECAM-1.

In some aspects, the shear stress/mechanical stretch is generated using a true linear motor. In some aspects, the shear stress/mechanical stretch is applied using a waveform. In certain aspects, the waveform is a dynamic mechanical loading waveform. In certain aspects, the dynamic mechanical loading waveform is a brachial waveform. In certain aspects, the waveform is a sine waveform. In some aspects, the dynamic mechanical loading waveform has a frequency of 0.1 Hz-1.00 Hz. In some aspects, the dynamic mechanical loading waveform has a magnitude of strain of from 0.1% to 17.5%.

In some aspects, at least 10 individual culture conditions are tested simultaneously. In some aspects, at least 100, 200, 300, 40, 500, or 600 individual culture conditions are tested simultaneously.

In some aspects, the methods further comprise (e) obtaining from the patient a starting population of mesenchymal stem cells (MSCs); (f) culturing the MSCs on a flexible surface that allows cell adhesion; and (g) applying the conditions identified following step (d) to the MSCs, thereby producing a therapeutically effective amount of MSCs having a combined pericyte/endothelial character. In certain aspects, the methods further comprise administering the conditioned MSCs to the patient.

In one embodiment, provided herein are compositions of mesenchymal stem cells (MSCs) having a combined pericyte/endothelial phenotype produced by the method of any of the present embodiments. In some aspects, the cells are not genetically modified. In some aspects, the pericyte phenotype is a type 2 pericyte phenotype. In some aspects, the cells express NG2. In some aspects, the cells can form myotubes or endothelial-like tubule structures. In some aspects, the cells have increased YAP/TAZ activation and increased SMAD2/3 activation. In some aspects, the cells have increased expression of endothelial markers and increased expression of pericyte markers. In certain aspects, the endothelial markers comprise PECAM-1, CD105, and VECad. In certain aspects, the pericyte markers comprise CD146, Nestin, PDGFRβ. In some aspects, the cells produce pro-angiogenic paracrine factors.

In one embodiment, provided herein are methods of treating a patient in need thereof comprising administering a therapeutically effective amount of a composition of any one of the present embodiments to the patient. In some aspects, the patient has a cardiovascular disease, is receiving vascular grafts, has ischemia, is wound healing, has peripheral ischemia, or has peripheral vascular disease. In some aspects, administering comprises injecting or implanting the cells into the patient.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the inherent variation in the method being employed to determine the value, the variation that exists among the study subjects, or a value plus or minus 5% of the stated number.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-G. High throughput system for applying mechanical forces to cultured cells. (FIG. 1A) The system applies mechanical strain to cells cultured in a 96 well plate format. A platen with 576 pistons is moved by a linear motor to displace a flexible membrane in six 96-well plates with flexible culture surfaces. (FIG. 1B) The culture plate consists of two plates that connect to hold a thin silicone membrane that serves as a culture surface. Thicker silicone membranes serve to seal each well and prevent leakage between the wells. Teflon pistons mounted on the platen are displaced into the membrane to apply mechanical strain to the cells cultured in each well. (FIG. 1C) Top view of the system showing the relative geometry of the piston and the culture surface. (FIG. 1D) Average strain applied by the system with vertical displacement of the platen. Each motor count is 10 μm of vertical displacement. (FIG. 1E) Well-by-well calibration of the individual wells of the system for a 96-well plate. (FIG. 1F) Dynamic strain waveforms produced by the system through control of the platen motion with the linear motor. The aortic and brachial waveforms simulate the strain on the arterial wall during the cardiac cycle in the body. (FIG. 1G) Computational simulation of the flow produced in the system by the motion of the piston shows that low levels of shear stress are created during the loading of the cells.

FIG. 2A-I. Mechanotransduction in MSCs is dependent on the magnitude and frequency of mechanical loading. (FIG. 2A) Transcription factor activity in MSCs was measured using a luciferase reporter assay after the application of cyclic mechanical strain for 8 hours with co-treatment with 10 ng/ml VEGF-A or 10 ng/ml TGF-β. *p<0.05 versus static control group. †p<0.05 versus static growth factor treated group. ‡p<0.05 versus control group under the same mechanical loading conditions. (FIG. 2B) Thin shims were added to adjust the height of the pistons to apply varying mechanical strain across the plate. (FIG. 2C) Diagram of one row of pistons displacing the membranes. When the lowest piston is applying 2.5% strain the highest piston is applying 17.5% strain. (FIG. 2D) Experimental calibration of the strain with the multi-strain configuration. (FIG. 2E) Smad transcription factor activity in MSCs with application of load for 24 hours using the multi-strain configuration. *p<0.05 versus static control group. †p<0.05 versus static growth factor treated group. ‡p<0.05 versus control group under the same mechanical loading conditions. (FIGS. 2F-G) The MSCs were treated with mechanical load using the multistrain format at 0.1 Hz for 24 hours and then immunostained for markers of vascular cell differentiation or signaling pathway activation. (FIG. 2F) Quantitative analysis of Yap/Taz nuclear localization and p-Smad2/3 activation after mechanical loading for 24 hours. In the top left panel, the left column of each pair is "Nuclear" and the right column of each pair is "Cytoplasm." *p<0.05 versus static group. (FIG. 2G) Quantification of vascular cell markers and cytoskeletal components following mechanical loading for 24 hours. In the left panel, the left column of each pair is "PECAM" and the right column of each pair is "α-SMA." In the right panel, the left column of each pair is "Actin" and the right column of each pair is "Paxillin." *p<0.05 versus static group. (FIG. 2H) MSCs were treated with mechanical strain of 7.5% maximal magnitude at 0.1 Hz using the sine or brachial waveform of loading and lysed an immunoblotted for the indicated proteins. (FIG. 2I) Quantification of western blotting for vascular markers and signal activation. *p<0.05 versus static and sine groups.

(FIG. 3A) MSCs were treated with differentiation treatments for seven days and then immunostained for markers of Hippo pathway/TGF-β signaling and differentiation into vascular phenotypes. Markers included Actin, Paxillin, SMAD2/3, P-SMAD2/3, 1-4-3-3-ε, nuclear YAP/TAZ, cytoplasmic YAP/TAZ, vWF, MyosinIIb, PECAM, αSMA, Sca-1, and Oct-4. Treatments included 5-azacytidine (5-Aza), dexamethasone and insulin (Dex/Ins), PDGF-BB, hydrocortisone (HC), EGF, VEGF-A, and TGF-β1. *p<0.05 versus cells treated with static conditions under baseline treatment. †p<0.05 versus mechanically strained group under baseline treatment. ‡p<0.05 versus cells under static conditions with the same biochemical treatment. (FIG. 3B) The cells were stained using Oil Red O or Alizarin Red dye to test for adipogenic and osteogenic differentiation.

FIGS. 4A-D. High throughput mechanobiological screen for small molecule inhibitors that have synergistic activation of Yap/Taz and Smad2/3 with mechanical loading. The MSCs were treated with 7.5% mechanical strain at 0.1 Hz for 24 hours in the presence of compounds from a library of kinase inhibitors. (FIGS. 4A-C) The cells were immunostained and quantified for nuclear localization of Yap/Taz (FIGS. 4A&B) and p-Smad2/3 staining (FIG. 4C). In FIG. 4A, the left column of each pair is "Control" and the right column of each pair is "Compound." In FIGS. 4B&C, the left column of each pair is "Static" and the right column of each pair is "7.5% Strain." *p<0.05 versus cells treated with static conditions under control treatment. †p<0.05 versus mechanically strained control group. (FIG. 4D) Overall summary of the screen showing the response distribution for the compounds. Labeled samples indicate the target of the inhibitor used or control treatments.

(FIG. 5A) Schematic representation of the assessment of the phenotype using multiple markers using flow cytometry. (FIG. 5B) Application of the schematic shown in FIG. 5A to assess the endothelial and pericyte phenotypes following stimulation. Included in the treatments were the pharmacological inhibitors identified in the high throughput screen for compounds that synergistically activated Smad2/3 and Yap/Taz nuclear localization. Within each triplet of columns, the left most is "Control," the middle is "Sine (7.5% Strain)," and the right most is "Brachial (7.5% Strain). " (FIGS. 5C-E) A tube formation assay was used to determine whether the cells under the different conditions had increased pericyte-like behavior and proangiogenic activity. Tube formation was tested using MSC conditioned media and endothelial cells (FIG. 5C), MSCs themselves (FIG. 5D), and MSCs mixed with endothelial cells (FIG. 5E). In FIGS. 5C-E, within each triplet of columns, the left most is "6 hours," the middle is "10 hours," and the right most is "22 hours. " (FIG. 5F) Mechanical loading of MSCs with the sine and brachial waveforms was performed and the conditioned media was tested in an endothelial proliferation assay. The loading on the cells was performed for seven days with conditioned media being collected each day. Y-axis represents relative proliferation. Within each pair of columns, the left column is "Static" and the right column is "5% Strain."

(FIG. 6A) Cells were conditioned with the various treatments for 7 days and then implanted them subcutaneously in nu/nu mice in Matrigel. After 14 days, the number of vessels invading the gels implanted with MSCs exposed to brachial waveform mechanical loading was determined based on macroscopic images of the implant. (FIG. 6B) The level of perfusion on the flanks of brachial waveform loaded MSCs was analyzed with laser speckle imaging. Within each triplet of columns, the left most is "Day 1," the middle is "Day 7," and the right most is "Day 14. " (FIG. 6C) Histological analysis of the gels to determine the levels of PECAM expression. (FIG. 6D) Histological analysis of the gels to determine the levels of CD146 expression.

FIGS. 7A-D. (FIG. 7A) A photograph of the PTFE pistons passing throughput a steel top plate. (FIG. 7B) The platen holds 576 pistons in a six by 96-well configuration. (FIG. 7C) Overview of the system with culture plates mounted. (FIG. 7D) Picture of the completed system.

FIGS. 8A-D. (FIG. 8A) Optimization of the mesh size and tolerance for the simulation. Shown is the average shear stress on the culture surface for a loading frequency of 1 hz and a maximum of 5% strain. (FIG. 8B) Peak flow rates within the well during application of mechanical strain. (FIG. 8C) Peak flow rates near the culture surface during application of mechanical strain. (FIG. 8D) Peak flow rates at the centerline within the well during application of mechanical strain.

DESCRIPTION

Figure 1E:
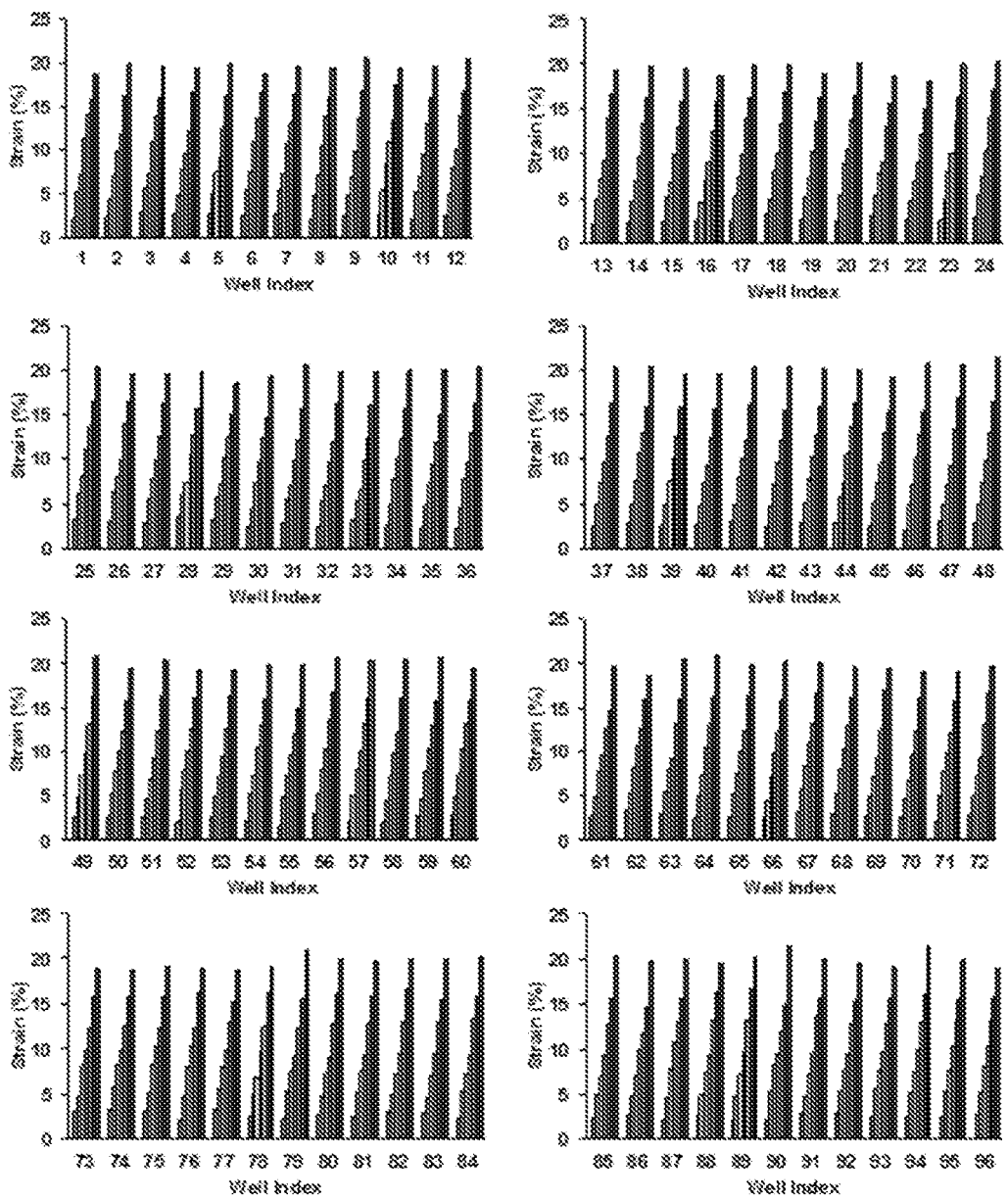

Mesenchymal stem cell (MSC) therapies are an emerging therapeutic approach with great potential to address many diseases not treatable by current technologies. While this is a promising approach, clinical trials suggest that current approaches to MSC therapy remain limited by poor or unreliable efficacy of the treatments. An assay that identifies specific conditions that enhance the therapeutic potential of MSCs for inducing therapeutic angiogenesis for treating ischemia and non-healing wounds has been developed. In addition, this approach has identified optimal conditions that induce MSCs to adopt a phenotype that has enhanced angiogenic activity.

A high throughput biaxial loading device (U.S. Pat. Publn. No 2014/0273210, which is incorporated herein by reference in its entirety) was used to discover optimal biomechanical conditions and drugs that can enhance mesenchymal stem cell (MSC) therapies for ischemia. This work has identified a novel mechanical loading waveform that enhances the pericyte and endothelial character of MSCs, enhancing their ability to induce angiogenesis when implanted. In addition, a drug screening assay was performed and drugs were found that act synergistically with mechanical loading to enhance the therapeutic potential of MSCs.

Mesenchymal stem cell therapy is a promising therapeutic technique that involves harvesting cells from the bone marrow or adipose tissue and injecting or implanting these cells. While this is a promising technique that is fairly easy to apply in clinical practice, the treatment has not achieved consistent results in clinical trials performed on patients who have had myocardial infarction (heart attack). There are several key issues that limit MSC therapies including poor phenotypic control of the cells, heterogeneity within the MSC population and the loss of therapeutic potential of the patient's MSCs due to aging and disease. Using the drug screening assay with mechanical loading in the biaxial loading system, optimal conditions that enhance MSC therapies have been developed. In addition, the assay enables the development and discovery of patient-specific biomechanical, biochemical and pharmacological conditions that enhance MSC therapies. For example, MSC therapies could be enhanced in a process with the following steps:

(1) Harvest MSCs from the patient;
(2) Perform biochemical/biomechanical screen for conditions that optimize markers for pericytes, endothelial cells and/or signaling pathways that correlate with enhanced therapeutic potential in MSCs;
(3) Treat large numbers of MSCs with the optimal conditions;
(4) Implant or inject MSCs to treat disease.

This approach will enhance MSC therapies by identifying the conditions that optimize MSC phenotype for treating disease. It also addresses the issue that MSCs from different patients respond differently and creates an optimal in vitro condition for each person's MSCs. General conditions for enhancing angiogenic potential in MSCs, which consists of a biomechanical waveform of mechanical loading and one of several drugs that target the EGF receptor and ErbB or PKC, have been identified. These conditions create a combined pericyte and endothelial phenotype in MSCs, a phenotype that has not been described previously and has enhanced regenerative properties.

I. ASPECTS OF THE INVENTION

Understanding mechanical regulation of cell signaling pathways and differentiation is crucial in many fields. There have been a number of devices that have been developed to apply and emulate the mechanical forces that are native to cells (Brown, 2000; MacQueen et al., 2013). However, the lack of throughput has been a major hurdle in efficiently studying the various facets of cellular signaling and enabling the rapid exploration of a wide variety of mechanical loading conditions. Moreover, interfacing mechanobiology with modern drug discovery and genome-wide screens would provide benefits in both academic and industrial studies. High-throughput systems for applying shear stress to cells in a multi-well/multi-channel formats have been recently developed (Voyvodic et al., 2012; Spruell & Baker, 2013; Spencer et al., 2015), and the system developed in this disclosure provides a parallel system for the high-throughput investigation of the response to mechanical strain. However, the system presented here has the advantages including the use of standard well format, modularity and improved dynamic control through the use of true linear motor. These enhancements enabled the system to perform drug screening with mechanical forces and to screen many mechanical strains simultaneously in optimizing mechanical conditioning for MSCs.

In these studies, the high throughput screening system was used to rigorously define the conditions that maximally increase activation of Hippo and Smad2/3 signaling. The signaling response in both these pathways was highly sensitive to both the magnitude and frequency of loading, with a maximal response at 7.5% strain and 0.1 Hz. In addition, a set of biochemical conditions combined with mechanical loading was screened and only limited differentiation toward the endothelial and vSMC phenotypes was found. A screen for activation of both Yap/Taz and Smad2/3 in combination with mechanical loading was performed and a set of compounds was found that enhanced both simultaneously. In addition, a comparison of the sine waveform to brachial waveform revealed increased expression of endothelial markers with the more dynamically complex brachial waveform. The combinations of brachial loading and the inhibitors caused a dramatic increase in the EC/pericyte phenotype. As screening was performed to maximize signaling pathway activation, this ultimately also enabled maximal differentiation towards this mixed phenotype. Thus, this work has the unexpected finding that maximizing the activation of these two pathways leads to the mixed EC/phenotype with enhanced regenerative properties.

Previous studies have identified that mechanical forces can increase the vascular cell phenotype of MSCs. Notably, the application of mechanical strain to MSCs increases expression of vSMC markers, and the application of shear has in some studies been linked to the expression of endothelial cell markers. The endothelial differentiation of MSCs is somewhat controversial, with some studies claiming differentiation into endothelial phenotype with VEGF-A treatment while others do not show these effects. Given the variation in behavior in MSC lines and heterogeneity in the MSC populations, these findings may both be true for the cells used in the studies. Much of the work examining endothelial cell differentiation in MSCs has used immunostaining or other methods that can only look at a few markers and have not, in general, examined the heterogeneity of the population. In this study, a flow cytometry technique, which aimed to define vascular cell phenotypes by using multiple markers and not excluding the possibility that the cells could express multiple phenotypes, was used. The analysis revealed the existence of a previously undescribed mixed pericyte/endothelial cell phenotype, which was enhanced through treatment with the brachial waveform of loading and further increased with co-treatment with small molecule inhibitors of EGFR/ErbB and EGFR/PKC.

Very little "true" endothelial cell or pericyte phenotypes were identified, as defined through multiple markers. While it is often hypothesized that endothelial differentiation of MSCs will improve the regenerative capabilities of the cells, this has not been shown, and given the short residence time of MSCs in clinical therapies, it is likely that paracrine mechanisms may be the primary mechanism of therapeutic effects in the current methodologies used for MSC-based treatments. The EC/pericyte phenotype described herein appears to have increased pericyte-like activity and paracrine effects on endothelial cells. This suggests that the pericyte component of the phenotype is primarily type 2, based on marker expression (Birbrair et al., 2013; Armulik et al., 2011), angiogenic properties, and the ability to form myotubes in culture (Birbrair et al., 2014). Thus, MSCs can be conditioned to have increased regenerative potential, even in the absence of genetic modification.

A key aspect and strength of the screening approach is that it addresses the fundamental limitation that MSCs from different patients and different sources may behave differently. MSCs could be harvested from patients and tested in a mechanobiological screen to optimize their signaling response and attainment of a mixed EC/pericyte phenotype. A second harvest of MSCs could then be performed, the cells conditioned with the optimal mechanical loading and biochemical/pharmacological treatments, and then implanted or injected into the patient for treatment. Thus, while the discovery of conditions that optimize the therapeutic activity of MSCs is a key finding and may be a generalizable approach, the proof of concept that a mechanobiological screen can be used to enhance MSC therapies and that a phenotype exists that improves their activity provides enhancement for MSC therapies for many applications.

II. METHODS OF TREATING

The term "cell population" is used herein to refer to a group of cells, typically of a common type. The cell population can be derived from a common progenitor or may comprise more than one cell type. An "enriched" cell population refers to a cell population derived from a starting cell population (e.g., an unfractionated, heterogeneous cell population) that contains a greater percentage of a specific cell type than the percentage of that cell type in the starting population. The cell populations may be enriched for one or more cell types and depleted of one or more cell types.

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs."

The term "pluripotent" refers to the property of a cell to differentiate into all other cell types in an organism, with the exception of extraembryonic, or placental, cells. Pluripotent stem cells are capable of differentiating to cell types of all three germ layers (e.g., ectodermal, mesodermal, and endodermal cell types) even after prolonged culture. A pluripotent stem cell is an embryonic stem cell derived from the inner cell mass of a blastocyst. In other embodiments, the pluripotent stem cell is an induced pluripotent stem cell derived by reprogramming somatic cells.

The term "differentiation" refers to the process by which an unspecialized cell becomes a more specialized type with changes in structural and/or functional properties. The mature cell typically has altered cellular structure and tissue-specific proteins.

As used herein, "undifferentiated" refers to cells that display characteristic markers and morphological characteristics of undifferentiated cells that clearly distinguish them from terminally differentiated cells of embryo or adult origin.

An "isolated" cell has been substantially separated or purified from others cells in an organism or culture. Isolated cells can be, for example, at least 99%, at least 98% pure, at least 95% pure or at least 90% pure.

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs)" are cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, and Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell.

A "therapeutically effective amount" used herein refers to the amount of a compound that, when administered to a subject for treatment of a disease or condition, is sufficient to effect such treatment.

Providing a therapy or "treating" refers to indicia of success in the treatment or amelioration of an injury, disease or condition, including any objective or subjective parameter such as abatement, remission, diminishing of symptoms of making the injury, disease or condition more tolerable to the patient, slowing the rate of degeneration or decline, making the final point of degeneration less debilitating, or improving a patient's physical or mental well-being. Those in need of treatment include those already with the disease or condition as well as those prone to have the disease or condition or those in whom the disease or condition is to be prevented. Preferred subjects for treatment include animals, most preferably mammalian species, such as humans and domestic animals such as dogs, cats, and the like, subject to the disease and other conditions. A "patient" refers to a subject, preferably mammalian (including human). Where the specification indicates that a number of cells are to be administered, a person of ordinary skill in the art will understand that these are approximate values.

In some embodiments, the dosage of the composition encompassing a therapeutically effective amount of mesenchymal stem cells ranges from $1.0 \times 10^3$-$1.0 \times 10^8$ cells/kg (weight). In some embodiments, the dosage ranges from $1.0 \times 10^4$-$1.0 \times 10^7$ cells/kg (weight). In some embodiments, about $1.0 \times 10^3$ cells/kg, about $1.0 \times 10^4$ cells/kg, about $1.0 \times 10^5$ cells/kg, about $1.0 \times 10^6$ cells/kg, about $1.0 \times 10^7$ cells/kg or about $1.0 \times 10^8$ cells/kg are administered.

The dosage of the composition may vary depending on patient's weight, age, sex and symptoms, the dosage form of the composition to be administered, a method of administering the composition, and so on. The frequency of administration may range from one to several times. There may be one or more administration sites. The dosage per kg for non-human animals may be the same as that for human, or can be converted from the above-described dosage, for example, based on the volume ratio (for example, average value) between the diseased tissue of the human and animal subjects. Animals to be treated according to the present invention include human and other desired mammals, specific examples of which include humans, monkeys, mice, rats, rabbits, sheep, horses, cats, cows and dogs.

In accordance with the present invention, the diseases or conditions can be treated or prevented by intravenous administration of the mesenchymal stem cells described herein. In some embodiments, about 20 million, about 40 million, about 60 million, about 80 million, about 100 million, about 120 million, about 140 million, about 160 million, about 180 million, about 200 million, about 220 million, about 240 million, about 260 million, about 280 million, about 300 million, about 320 million, about 340 million, about 360 million, about 380 million, about 400 million, about 420 million, about 440 million, about 460 million, about 480 million, about 500 million, about 520 million, about 540 million, about 560 million, about 580 million, about 600 million, about 620 million, about 640 million, about 660 million, about 680 million, about 700 million, about 720 million, about 740 million, about 760 million, about 780 million, about 800 million, about 820 million, about 840 million, about 860 million, about 880 million, about 900 million, about 920 million, about 940 million, about 960 million, or about 980 million cells are injected intravenously. In some embodiments, about 1 billion, about 2 billion, about 3 billion, about 4 billion or about 5 billion cells or more are injected intravenously. In some embodiments, the number of cells ranges from between about 20 million to about 4 billion cells, between about 40 million to about 1 billion cells, between about 60 million to about 750 million cells, between about 80 million to about 400 million cells, between about 100 million to about 350 million cells, and between about 175 million to about 250 million cells.

In some embodiments, a single intravenous administration is sufficient, while in other embodiments, multiple intravenous administrations are performed, such as 2, 3, 4, 5, 6, 7, 8, 9 10, 11, 12, 13, 14, 15, 16, 17, 18, 19, or 20 intravenous administrations of the mesenchymal stem cells. The treatment interval(s) can be spaced such that an administration follows a prior administration by one day, 2 days, 3 days, 4 days, 5 days, 6 days, one week, 1½-2 weeks, 3 weeks, one month, or 2-3 months, 6 months, one year, or two years or longer. In some embodiments, the treatment interval is spaced in accordance with the progression of the patient's improvement or response to treatment. For example, in some embodiments, a first treatment is administered followed by a second treatment one week later, followed by a third treatment one month later, followed by a fourth treatment 6 months later.

The therapeutic methods of the present invention can be conducted alone or in combination with other standard or advanced methods or pharmaceutical treatments.

The therapeutic composition of mesenchymal stem cells for use in the methods of the present invention can comprise pharmaceutically acceptable carriers and/or additives. Examples thereof include sterilized water, physiological saline, a standard buffer (e.g., phosphoric acid, citric acid, or other organic acids), a stabilizer, salt, an antioxidant (e.g., ascorbic acid), a surfactant, a suspending agent, an isotonic agent, or a preservative. As used herein, the term "base" refers to a base solution in which the mesenchymal stem cells in the cell therapeutic composition are suspended. In some embodiments, physiological saline, phosphate buffered saline or Hartrnan-D (Choongwae Pharma Corp.) is used as the base solution.

In some embodiments, the cell therapeutic composition is prepared in a dosage form suitable for injection. In some embodiments, the mesenchymal stem cells are dissolved (suspended) in a pharmaceutically acceptable aqueous solution, or frozen in a solution state. The kit of the present invention may further comprise a desired pharmaceutically acceptable carrier that can be used to suspend or dilute the mesenchymal stem cells. Examples of such a carrier include distilled water, physiological saline, PBS and the like.

The composition for use in the present invention can contain a pharmaceutically acceptable carrier or excipient, or any necessary stabilizer or adsorption-preventing agent to provide a pharmaceutical preparation that is suitable for administration to humans or animals. The composition of the present invention can be formulated in the form of an injectable solution (e.g., injection solutions for subcutaneous, intradermal, intramuscular, intravenous and intraperitoneal injection). In some embodiments, upon the injection of the composition of mesenchymal stem cells, an analgesic agent, which can relieve pains, may be used.

The cell therapeutic composition of mesenchymal stem cells for use in the present invention can be filled into a syringe, a device, a cryovial in which cells can be frozen, or a pyrogen-free glass vial comprising rubber stoppers and aluminum caps, which contains liquid drugs.

The cell therapeutic composition of mesenchymal stem cells for use in the present invention can, if necessary, contain at least one selected from among suspending agent, solubilizing agents, stabilizers, isotonic agents, preservatives, adsorption-preventing agents, surfactants, diluents, vehicles, pH-adjusting agents, analgesic agents, buffering agents, sulfur-containing reducing agents and antioxidants, depending on the administration mode or formulation thereof.

Examples of the suspending agents may include methylcellulose, Polysorbate 80, hydroxyethylcellulose, gum acacia, gum tragacanth powder, sodium carboxymethylcellulose, polyoxyethylene sorbitan monolaurate, etc. The solubilizing agents include polyoxyethylene hydrogenated castor oil, polysorbate 80, nicotinamide, polyoxyethylene sorbitan monolaurate, Macrogol and castor oil fatty acid ethyl esters. The stabilizers include dextran 40, methylcellulose, gelatin, sodium sulfite, sodium metasulfite, etc. Examples of the isotonic agents are D-mannitol and sorbitol.

Examples of the preservatives include methyl parahydroxybenzoate, ethyl parahydroxybenzoate, sorbic acid, phenol, cresol, and chlorocresol. Examples of the adsorption preventing agents include human serum albumin, lecithin, dextran, ethylene oxide-propylene oxide copolymer, hydroxypropylcellulose, methylcellulose, polyoxyethylene hydrogenated castor oil, and polyethylene glycol.

The sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms.

The antioxidants include, for example, erythorbic acid, dibutylhydroxytoluene, butylhydroxyanisole, [alpha]-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate. The cryopreservatives include, for example, DMSO, glycerol, etc.

Furthermore, in some embodiments, the cell therapeutic composition of mesenchymal stem cells for use in the methods of the present invention can comprise conventional additives, such as inorganic salts, including sodium chloride, potassium chloride, calcium chloride, sodium phosphate, potassium phosphate and sodium hydrogen carbonate, and organic salts, including sodium citrate, potassium citrate and sodium acetate.

In some embodiments, sucrose or albumin is added to the mesenchymal stem cells to improve stability, prior to cold storage of the cells. In some embodiments, the cells are combined with physiological saline, sucrose, albumin and cryopreservative DMSO prior to freezing and cold storing the cells.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Construction of a high throughput biaxial oscillatory strain system. The system was created through standard machining techniques and was composed of 316L stainless steel, polycarbonate and aluminum. All pieces of the system in contact with culture media were of 316L stainless steel or polycarbonate. In the system, strain is applied to cells through the motion of a platen with 576 pistons mounted on it. The platen is displaced using a sealed, true linear motor (Copley Controls). To prevent generation of excess heat, a cooling flow system drives water from an external water bath (outside the incubator) through the motors. A platen is mounted on four motion rails with linear ball bearings. Fixed springs support the platen in the absence of current through the motor and provide static off-loading for the platen weight. On the platen are 576 individual PTFE pistons (5 mm diameter) that are replaceable and can be calibrated individually through the introduction of thin shims. Vegetable oil was used as a lubricant to prevent friction of the pistons with the silicone membrane. The top plate on the system has mounting holes for custom designed culture plates that hold a silicone membrane sandwiched between steel plates and silicone gaskets. The membranes were placed under repeatable pretension using a custom mounting jig/procedure. The culture plates are composed of upper and lower plates with 96 holes that exactly match the geometry of a standard 96 well plate. Between the plates, a silicone culture membrane is sandwiched between two silicone seals that have the geometry of a 96 well plate and seal each well individually. The culture membrane was medical grade gloss/gloss silicone with thickness of 0.005" (Specialty Manufacturing, Inc.). The plates are sterilized prior to cell seeding by UV light and are coated by treatment with 50 µg/mL fibronectin at 37° C. overnight.

Calibration of mechanical strain on the silicone membrane. Mechanical strain applied to the flexible membrane was measured by recording the movement of marks created on the silicone membrane. The piston was displaced at small increments through the membrane and a high magnification image of the mark was recorded using a high-resolution camera (Basler). The marker displacements from the captured video were measured using Metamorph Imaging software. Membrane was displaced in sinusoidal, aortic, and brachial waveforms created from clinical arterial distension data. For each waveform, three cycles of the waveform were recorded and averaged.

Computational modeling of flow within the system. Fluid mechanics in the cell culture media with the displacement of a circular cross section piston was modeled using finite element software (COMSOL). Briefly, a cylindrical shape fluid structure was used to model a single well with viscosity and density of standard DMEM media. The bottom surface was displaced in a sinusoidal motion over time with three frequencies (0.1 Hz, 1 Hz, and 2 Hz) in combination with three maximum magnitudes (1%, 5%, and 10%). A series of mesh and tolerance optimization were performed to optimize these parameters. Maximum and average fluid velocity at various cross sections was computed. Average shear stress in various locations and over various time points were computed as well with the focus on the location of the bottom surface undergoing displacement where the cells are located. To aid in understanding the forces applied by the piston designed for uniaxial remodeling, a model of the silicone membrane being displaced by this piston was created. For uniaxial loading, membrane strain was computed under stationary solid mechanics module of COMSOL. A PTFE piston model with two prongs was displaced at set increments through a thin flexible silicone membrane and the strain in the membrane calculated.

HMSC culture method. Human mesenchymal stem cells (hMSCs; Millipore) were cultured in low glucose DMEM medium supplemented with 15% fetal bovine serum, L-glutamine, and penicillin/streptomycin. Following trypsinization, cells were seeded on the membranes at 4,000 cells per $cm^2$ before mechanical loading.

Transcription factor activity assay. The cells were transduced with luminescent reporter vectors for target transcription factors. Briefly, for each target transcription factor, freshly passaged hMSCs were treated with luciferase reporter expressing lentiviruses (Qiagen). For the drug screening assay, hMSCs were treated with biomolecules in the kinase inhibitor library (Millipore Calbiochem) 1 hour prior to loading. After mechanical loading, the cells were lysed and the relative luminescent signal was measured using the luciferase assay kit (Promega) with FlexStation-3 plate reader (Molecular Devices). For each plate, average from three individual readings was reported.

Immunocytochemical staining. Cells were fixed in 4% paraformaldehyde in PBS for 10 min followed by washing and permeabilization with 0.1% Triton X-100 PBS for 5 min. Next, samples were blocked with 1% BSA 5% FBS in PBS for 40 min. After washing, cells were incubated with primary antibodies (Table 1) overnight at 4° C. The next day, samples were washed in 1% BSA in PBS and was incubated with secondary antibodies and DAPI staining for 2 hours in a light protected environment. For actin staining, an alternative step was used in which samples were treated with Alexa 594 conjugated phalloidin for 30 min. Cells were washed thoroughly before they were imaged. For standard fluorescent microscopy, Zeiss Observerl was used. For confocal imaging, Zeiss Axiovert FLM of UT Austin ICMB and Olympus Fluoview of Institute for Biomaterials, Drug Delivery & Regenerative Medicine of UT Austin were used.

TABLE 1

Primary antibodies used for immunostaining.

| Target Protein | Company | Catalog # | Species/Isotype | Dilution Ratio |
|---|---|---|---|---|
| AF 594 Phalloidin | Invitrogen | A12381 | N/A | 1:250 |
| Paxillin | Santa Cruz Biotechnology | sc-5574 | anti-rabbit | 1:50 |
| PECAM-1 | Cell Signaling | 3528S | anti-mouse | 1:100 |
| α-SMA | Abcam | ab21027 | anti-rabbit | 1:100 |
| ILK | BD Biosciences | 611803 | anti-mouse | 1:100 |
| YAP/TAZ | Cell Signaling | 8418S | anti-rabbit | 1:100 |
| 14-3-3-ε | Santa Cruz Biotechnology | sc393177 | anti-mouse | 1:50 |
| Smad 2/3 | BD Biosciences | 610842 | anti-mouse | 1:100 |
| Phospho-Smad 2/3 | Cell Signaling | 8828S | anti-rabbit | 1:100 |
| vWF | Santa Cruz Biotechnology | 365712 | anti-mouse | 1:50 |
| Myosin IIb | Cell Signaling | 3404 | anti-rabbit | 1:100 |
| Sca-1 | Santa Cruz Biotechnology | sc-365343 | anti-mouse | 1:50 |
| Oct-4 | Cell Signaling | 2750 | anti-rabbit | 1:100 |

Immunoblotting. Following mechanical loading, the cells were assayed by western blotting. Briefly, cells were lysed in 20 mM Tris with 150 mM NaCl, 1% Triton X-100, 0.1% SDS, 2 mM sodium orthovanadate, 2 mM PMSF, 50 mM NaF, and protease inhibitors. Lysates were run on NuPAGE 10% bis-tris midi gel (Novex) and transferred to nitrocellulose membrane using iBlot transfer stack (Novex). The membranes were blocked for 1 hour in 5% non-fat milk in PBS with 0.01% tween-20 (PBST) and exposed to primary antibodies (Table 2) in 4° C. overnight in 1% non-fat milk. The membranes were washed with PBST, and incubated at room temperature for 2 hours with secondary antibody. The membrane was imaged using chemiluminescence camera (Cell Biosciences) after treating the membranes with SuperSignal West Femto chemiluminescent substrate (Thermo Scientific).

TABLE 2

Primary antibodies used for immunoblotting.

| Target Protein | Company | Catalog # | Species/Isotype | Dilution Ratio |
|---|---|---|---|---|
| GAPDH | Cell Signaling | 2118S | anti-rabbit | 1:500 |
| PECAM-1 | Cell Signaling | 3528S | anti-mouse | 1:500 |
| α-SMA | Abcam | ab21027 | anti-rabbit | 1:500 |
| Smad 2/3 | BD Biosciences | 610842 | anti-mouse | 1:500 |
| Phospho-Smad 2/3 | Cell Signaling | 8828S | anti-rabbit | 1:500 |
| Phospho-β Catenin | Abcam | ab27798 | anti-rabbit | 1:500 |

Long term conditioning of hMSCs using biochemical factors. For long term loading, cells were exposed to media containing small biomolecules (Table 3). They were loaded for 4 hours every day for 7 days under sine and brachial waveform at 0.1 Hz and 7.5% maximum strain and compared against those in static culture. Media containing the biomolecules were replaced on day 3 and day 5, with the exception of 5-Aza containing media. Due to the cytotoxic nature of 5-Aza, it was replaced with normal media on day 1. On day 6, media was replaced with 0.5% FBS containing media post loading. Following long term loading on day 7, the condition media was collected and further assays were performed on the cells.

TABLE 3

Reagents for treating cells in long-term loading.

| Biomolecule | Company | Catalog # | Concentration |
|---|---|---|---|
| 5-Azacytidine | Sigma-Aldrich | A2385 | 2.44 μg/mL |
| Dexamethasone | Sigma-Aldrich | D4902 | 10 nM |
| Insulin | Sigma-Aldrich | 13536 | 10 ug/mL |
| PDGF-BB | PeproTech | 100-14B | 10 ng/mL |
| Hydrocortisone | Sigma-Aldrich | H0888 | 10 mM |
| EGF | Sigma-Aldrich | E9644 | 10 ng/mL |
| VEGF | PeproTech | 100-20A | 10 ng/mL |
| TGF-β1 | PeproTech | 100-21 | 10 ng/mL |

Fluorescence Activated Cell Sorting (FACS). After long term loading, the cells were then detached from the loading plate using accutase (Sigma) and was labeled with fluorescent antibodies according the BD Bioscience FACS staining kit (BD 562725) for cardiovascular phenotypes such as endothelial, smooth muscle, and pericyte phenotypes. (Table 4). Fortessa of UT Austin Core Facility was used to measure population fluorescent signals.

TABLE 4

List of primary antibodies used for FACS

| Target Protein | Company | Catalog # | Fluor. Dye |
|---|---|---|---|
| PECAM-1 | BD Biosciences | 562855 | BV605 |
| VE-Cadherin | BD Biosciences | 565671 | BV421 |
| CD146 | BD Biosciences | 564644 | FITC |
| PDGFR-β | BD Biosciences | 558821 | PE |
| CD105 | BD Biosciences | 563466 | BV650 |
| Nestin | BD Biosciences | 561231 | PerCP/Cy5.5 |

Tube formation assay. A day prior to tubule formation assay, Growth factor reduced Matrigel (Corning 354230) was allowed to thaw overnight at 4° C. HUVEC cells were labeled with cell tracker red (LifeTech C34552) and hMSC cells were labeled with cell tracker green (LifeTech C7025). These cells were then cultured in serum starved 0.5% FBS containing media 16 hours prior to the tubule formation assay. On the day of the assay, glass bottom plates were coated with thin Matrigel and was incubated at least 30 minutes at 37° C. The fluorescently labeled cells were passaged with the conditioned media from the long term loading onto the plates at a total seeding density of 20,000 cells/well in either hMSC alone, HUVEC alone, or a co-culture of both hMSC and HUVEC at 1:1 ratio. These cells were then imaged at 0 hour, 10 hours, and 22 hours post seeding using Cytation 5 at UT Austin Targeted Therapeutic Drug Discovery & Development Program (TTP). For quantification, number of complete loops formed was counted.

Subcutaneous matrigel-cell injection on Nu/Nu mice. To assess the in vivo response of conditioned hMSCs, subcutaneous injection on Nu/Nu mice model was used. Briefly, following long term conditioning, the cells were detached from the loading plate using 0.05% Trypsin-EDTA and spun down at 200 g for 3 min. Next, the supernatant was removed and the cells were resuspended in Matrigel (Corning 356237) at $2 \times 10^6$ cells/mL. These cell suspensions were then injected into the dorsal back of the 6 weeks old Nu/Nu mice on either left or the right side at 200 uL to create Matrigel plugs containing conditioned hMSCs. Blood flow through the back of the mice were assessed using Speckle Imaging developed by Dr. Andrew Dunn of University of Texas at Austin for day 1, day 3, day 5, day 7, and day 14. On day 14 post injection, the mice were euthanized, and the skin tissues containing the Matrigel plugs were imaged and fixed using 10% formalin for further assays.

All animal studies were performed with the approval of the University of Texas at Austin Institutional Animal Care and Use Committee (IACUC) and in accordance with NIH guidelines "Guide for Care and Use of Laboratory Animals" for animal care.

Immunohistochemistry and Fluorescent Tissue Staining. Sections of fixed skin tissues were submerged in 30% sucrose in PBS for 4 days post fixing. Next, the tissue samples were frozen in isopentane and were sliced at 10 µm and 20 µm thick tissue slices. H&E staining was done on the 10 µm thick tissues, while fluorescent imaging was done on 20 µm thick using the antibodies found in Table 5 and were imaged using confocal microscopy Olympus Fluoview of Institute for Biomaterials, Drug Delivery & Regenerative Medicine of UT Austin.

TABLE 5

List of primary antibodies used for tissue immunostaining

| Target Protein | Company | Catalog # | Species/ Isotype | Dilution Ratio |
| --- | --- | --- | --- | --- |
| Mitochondria Human | Millipore Calbiochem | MAB1273 | anti-mouse IgG1 | 1:100 |
| PECAM | Abcam | ab28364 | anti-rabbit | 1:100 |
| αSMA | Abcam | ab21027 | anti-goat | 1:100 |
| PDGFRB | Santa Cruz Biotechnology | sc-374573 | anti-mouse IgG2a | 1:50 |
| CD146 | Abcam | ab75769 | anti-rabbit | 1:100 |
| Nestin | Santa Cruz Biotechnology | sc-377380 | anti-mouse IgG2a | 1:50 |
| Ki67 | Abcam | ab15580 | anti-rabbit | 1:100 |

Measurement of soluble factor production. Cell culture media were collected from 24 hours of stretching at 7.5% for 0.1 Hz and from the long term conditioning loading. Soluble factors and paracrine signaling in these media were measured using ELISA kit per manufacturer's instructions.

Statistical analysis. All results are shown as mean±standard error of the mean. Multiple comparisons between groups were analyzed by two-way ANOVA followed by a Tukey post-hoc or a Dunnett post-hoc test when testing multiple comparisons versus a control group. A p-value of 0.05 or less was considered statistically significant.

Example 1—High Throughput System for Studying Stem Cell Mechanobiology

Figure 1F:
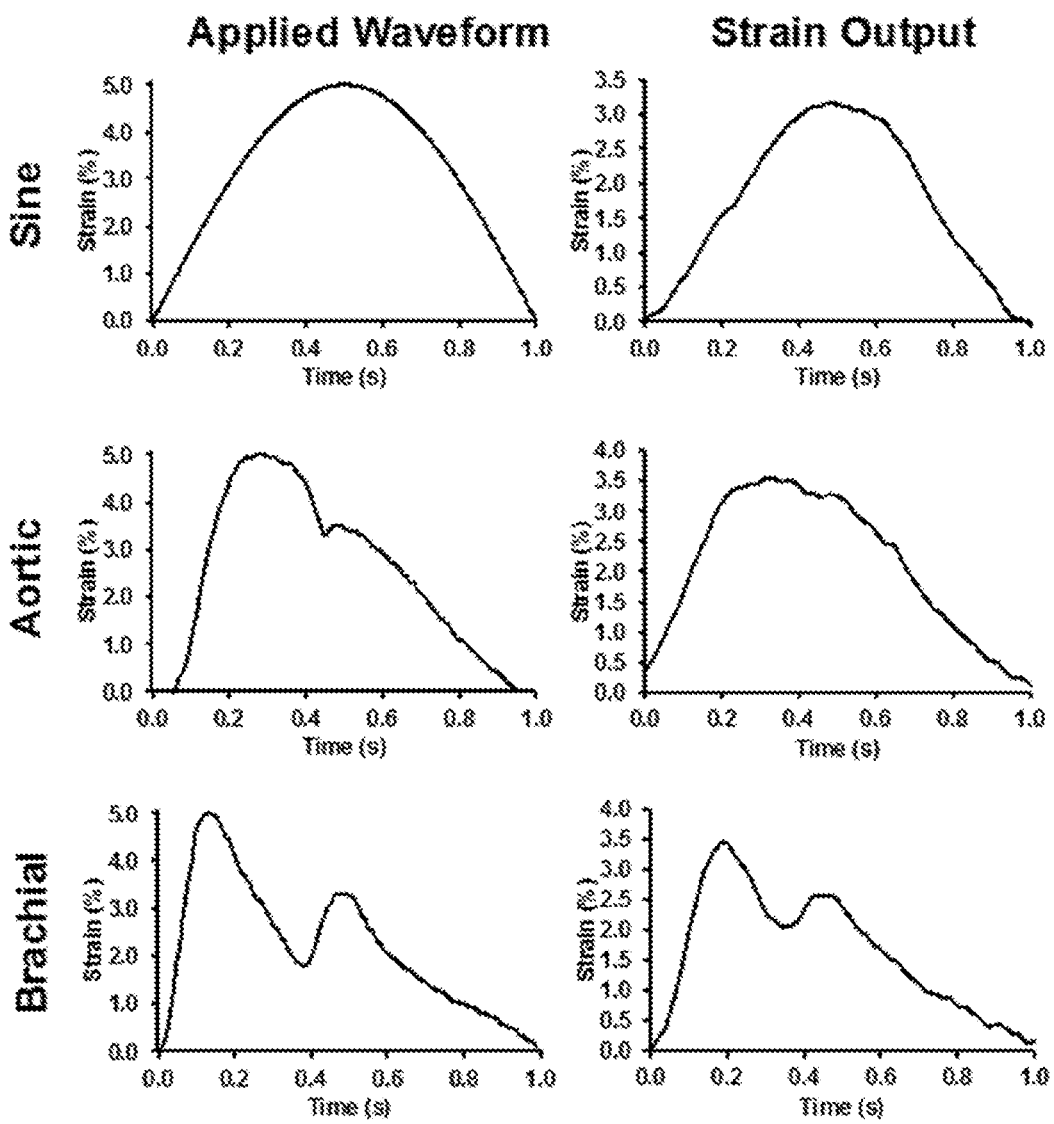
Figure 1G:
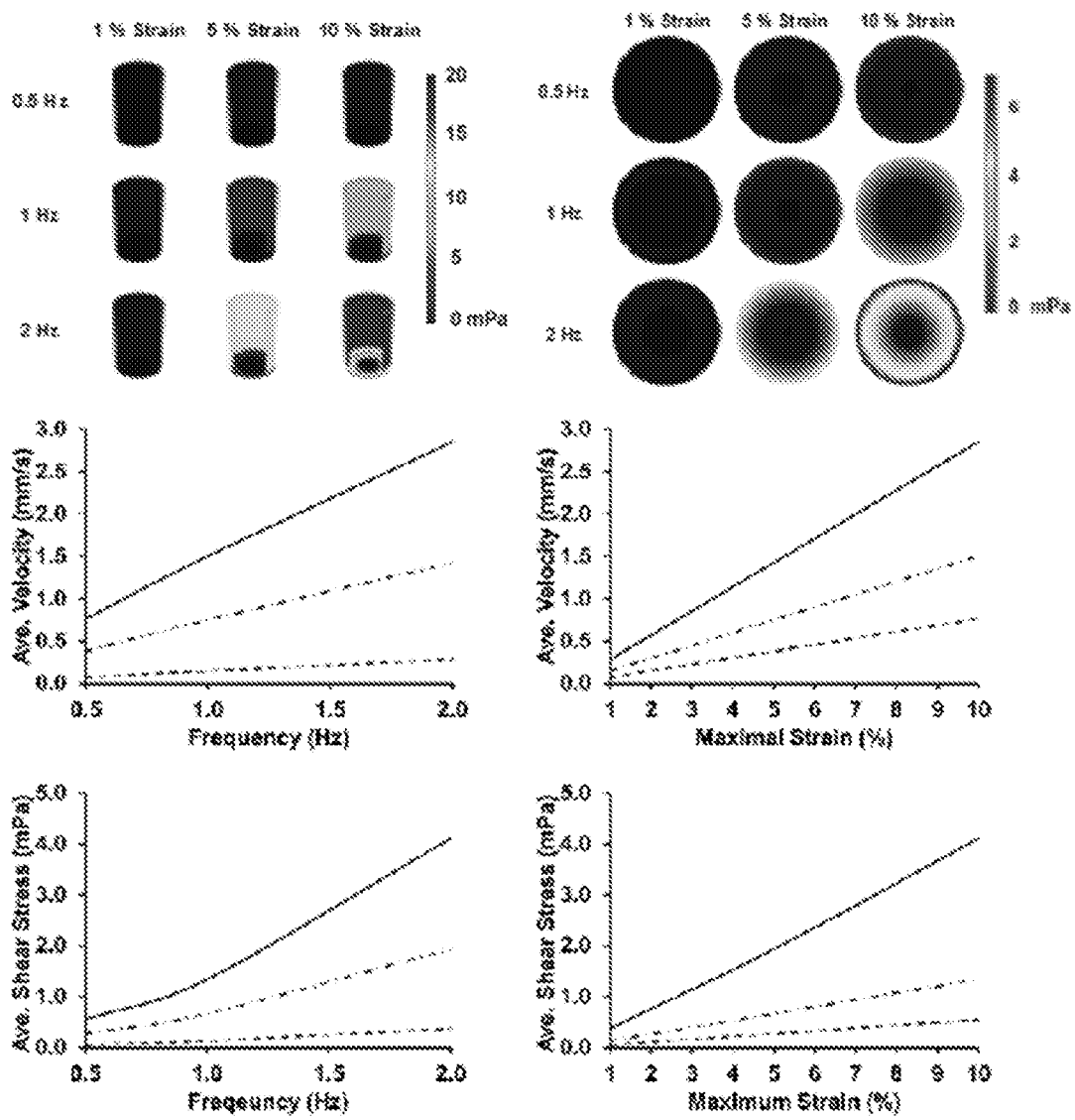

The inventors created a high throughput mechanical loading system that allows the application of mechanical stretch to culture cells in six 96-well plates simultaneously. The system works on the principle of displacing an array of pistons through a flexible bottom culture plate. The high throughput biaxial oscillatory strain system (HT-BOSS) drives the motion of a platen using a true linear motor (FIG. 1A; FIGS. 7A-D). Teflon pistons are mounted on the platen that can be driven to displace a flexible culture surface within a custom culture plate (FIG. 1B). In terms of applied strain, the HT-BOSS can apply strains based on the displacement of the piston (FIGS. 1C, D). Each of the pistons can be adjusted in height individually and extensive well-by-well calibration allowed the system to apply highly accurate and reproducible strains to each well (FIG. 1E). The true linear motor uses an electromagnetically controlled stator that allows customizable displacements to create complex dynamic strain waveforms. It was verified that the system can apply sine waveforms and two strain waveforms derived from the displacement of the arterial wall in the aorta and brachial arteries (FIG. 1F) (Lee et al., 2013). A computational model of the flow within the system due to the piston displacement was created and found that the shear stress created during loading was on the order of millipascals, similar to larger format systems, and dependent on the frequency and magnitude of the strain (FIG. 1G; FIGS. 8A-D) (Lee & Baker, 2015).

Example 2—Mechanical Regulation of Transcription Factor Activity and Signaling Pathways in Mesenchymal Stem Cells A major limitation of previous studies in mechanobiology is the limited ability to investigate a variety of conditions simultaneously. This gap in capability leads to an incomplete exploration of the range of mechanical conditions and greatly reduces the ability to examine synergy between applied mechanical forces and biochemical signals. Mesenchymal stem cells were transduced with lentiviruses expressing luciferase reporter constructs for transcription factors including FOXO, TCF/LEF, Smad2/3 and SRE and selected these to obtain a stable reporter cell line. Whether there was synergy between biochemical and biomechanical activation of the transcription factors was explored by exposing the cells to VEGF or TGF-β during mechanical loading. These two factors have been linked to stimulating differentiation in MSCs to vascular cell types and other lineages (Oswald et al., 2004; Janeczek Portalska et al., 2012; Tamama et al., 2008). For the transcription factor FOXO, no stimulation of transcription factor activity was observed but a reduction in FOXO activity was found with VEGF treatment at 2 Hz frequency of loading (5% maximal strain) or with VEGF treatment at 1 Hz frequency of loading (FIG. 2A). In contrast, TCF/LEF was synergistically activated by loading at 0.1 Hz and VEGF treatment (FIG. 2A). The Smad2/3 transcription factors were also synergistically activated by loading at 0.1 Hz and suppressed by loading at 1 or 2 Hz (FIG. 2A).

Figure 2G:
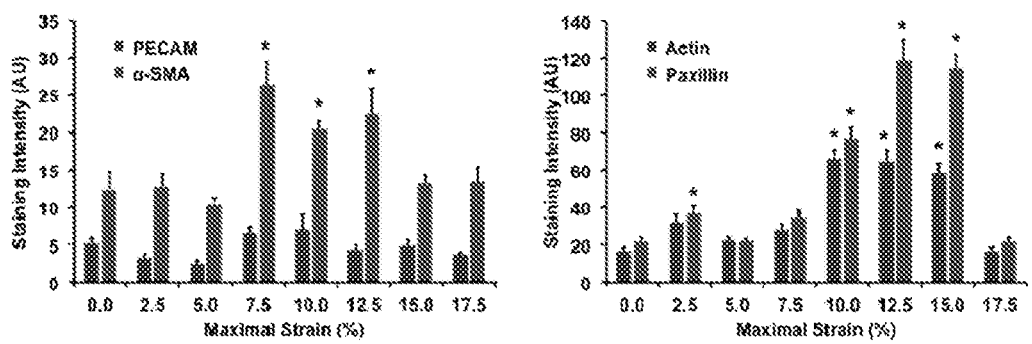
Figure 2H:
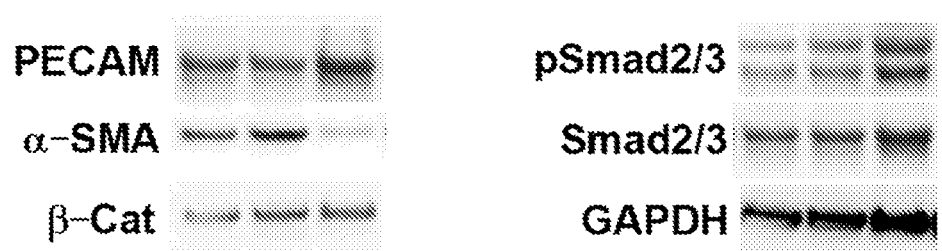
Figure 2I:
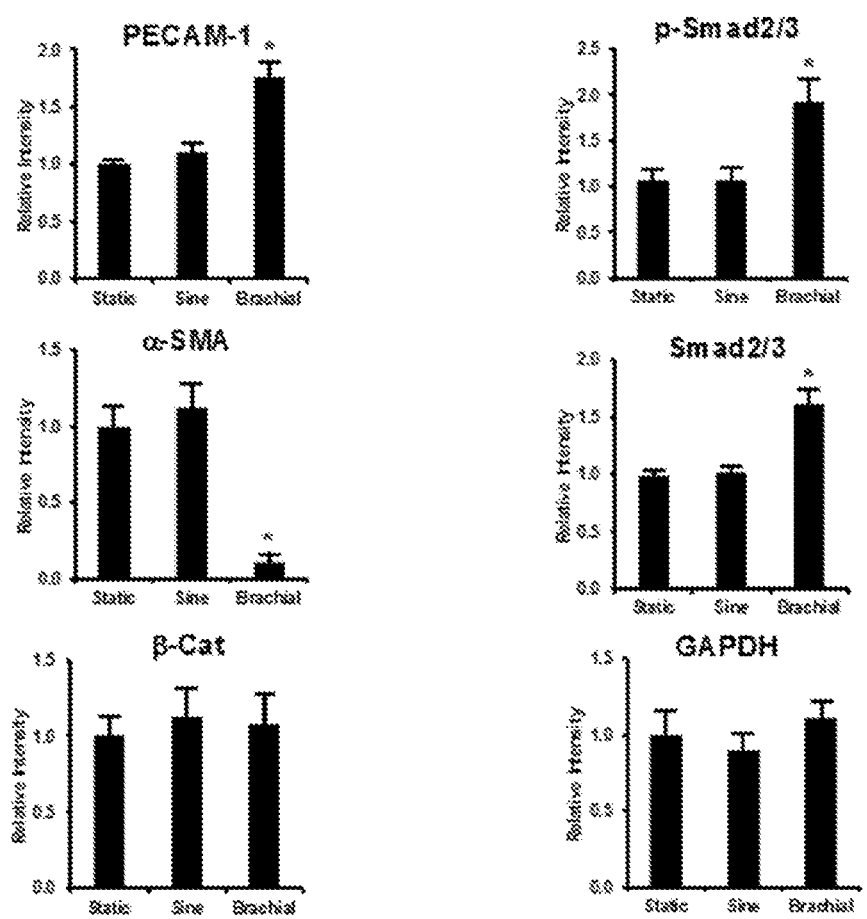

Example 3—Multi-Strain Mechanical Loading Assays Reveal Optimal Conditions for Smad2/3 Transcription Factor Activation and Regulation of Vascular Cell Markers in MSCs To perform a high throughput assay of the dependence of magnitude of mechanical strain on the activation of Smad2/3, the heights of the individual pistons were adjusted to apply mechanical strains over a range of 0 to 17.5% strain, in increments of 2.5% strain (FIGS. 2B-D). Mechanical strain was applied over this range at a frequency of 0.1 Hz, based on the frequency dependence experiments, and found optimal synergistic activation of Smad transcription factors at 7.5% strain with co-treatment with TGF-β1 (FIG. 2E). The regulation of differentiation-related pathways in MSCs was examined by loading the cells for 24 hours under multi-strain conditions at 0.1 Hz and performing immunostaining. A maximal increase in nuclear to cytoplasmic Yap/Taz was found at 7.5% strain and maximal nuclear localization of Smad2/3 at 10-12.5% strain (FIG. 2F). In addition, there was a maximal increase in α-SMA expression in the range of strains from 7.5-12.5% strain (FIG. 2G). At 10-15% strain, there was a maximal increase in polymerized actin and paxillin (FIG. 2G). The mechanical loading was repeated at 7.5% strain with 0.1 Hz frequency using both sine and brachial waveforms and then performed western blotting. With brachial waveform loading, increases in PECAM-1 expression were found and as well as a reduction in α-SMA expression and an increase in p-Smad 2/3 (FIGS. 2H, I). Overall, these studies support maximal activation of Smad signaling in MSCs with 0.1 Hz of loading at 7.5% strain, with an increase in endothelial-like phenotype with brachial loading.

Figure 3A:
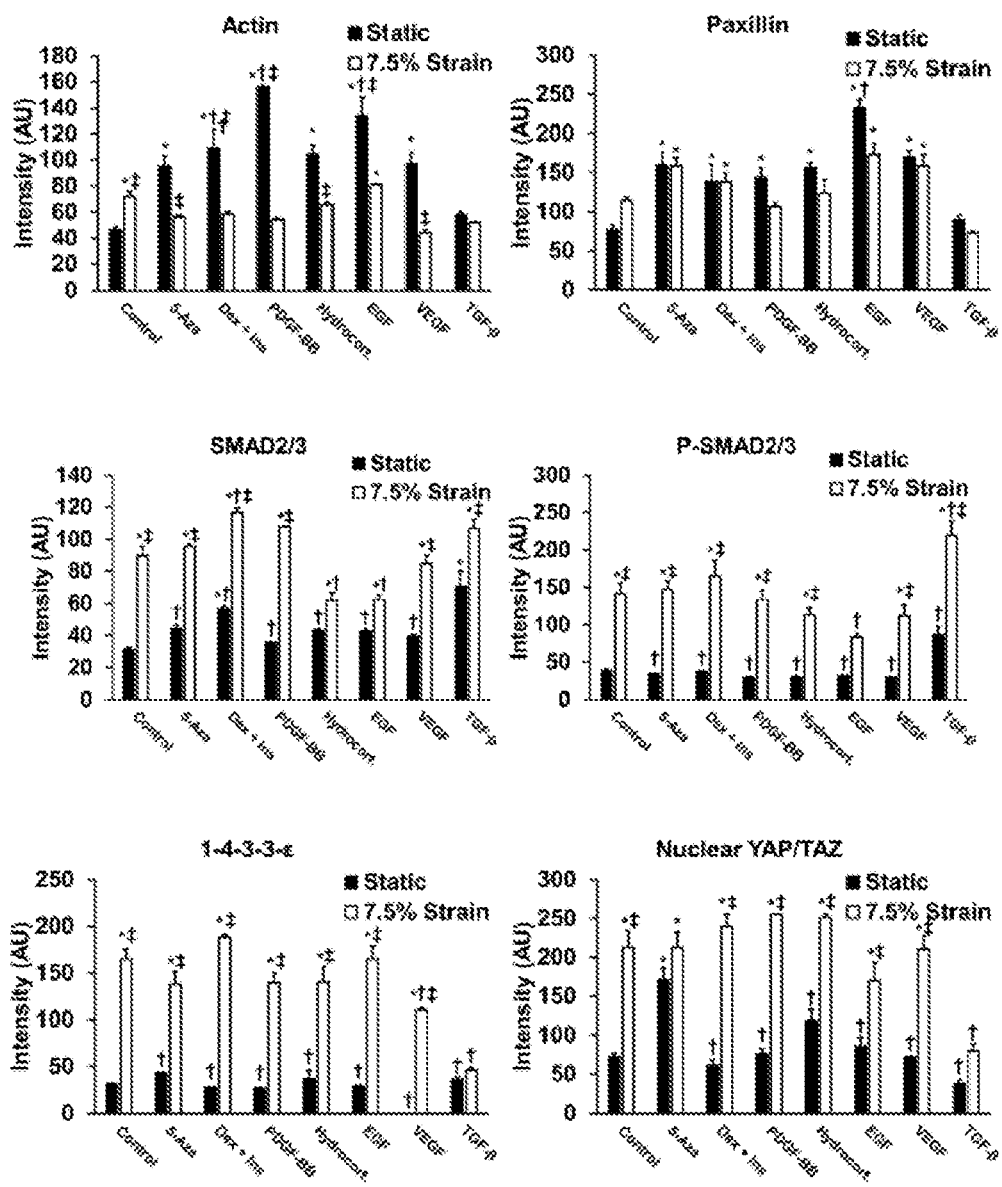
FIGS. 3A-B. Activation of mechanotransduction pathways and expression of vascular cell markers in mesenchymal stem cells under long-term treatment with biochemical differentiation treatments and mechanical loading.
Figure 3A:
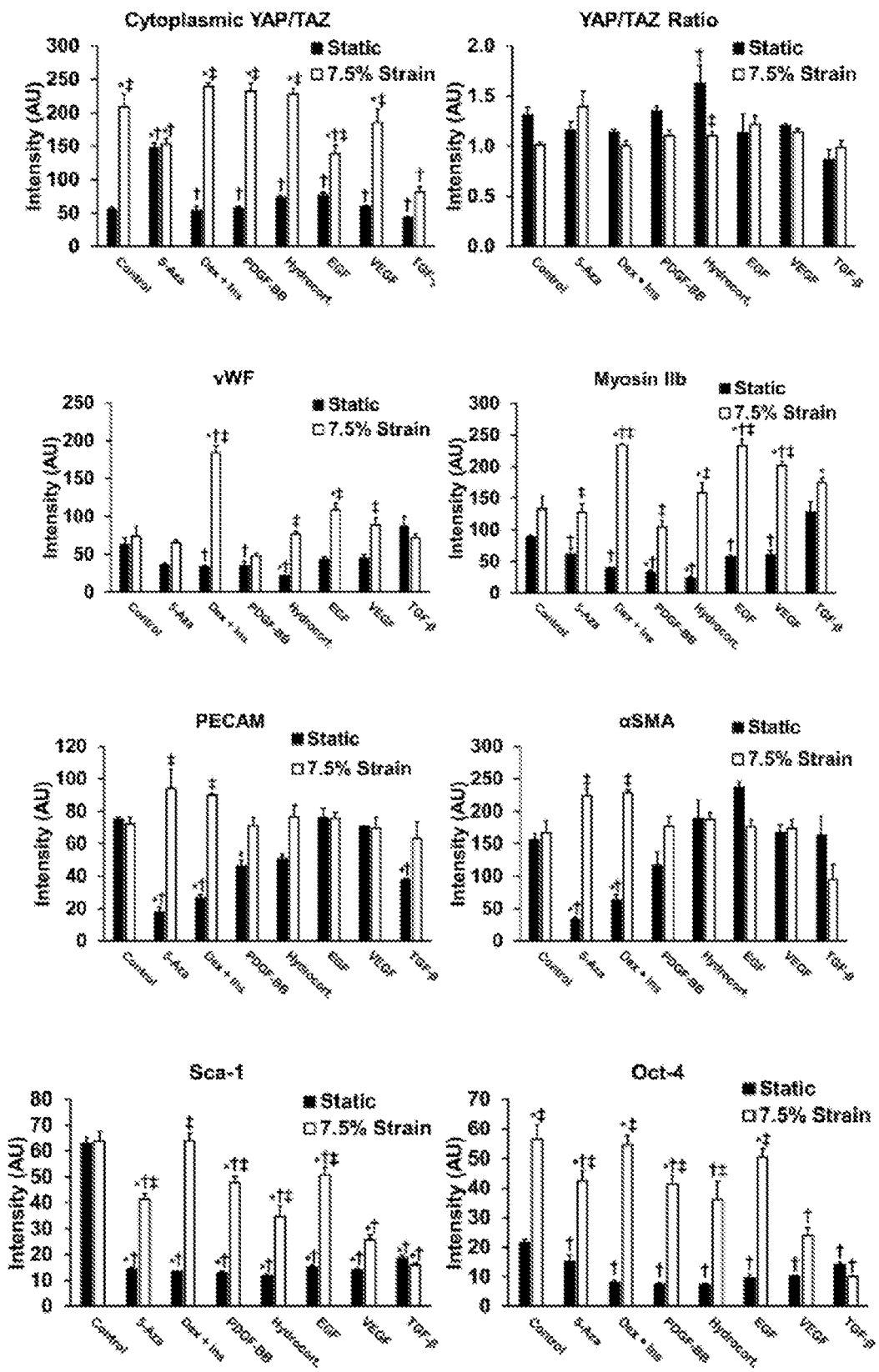

Example 4—Long-Term Treatment with Mechanical Load and Differentiation Factors Regulates Pluripotency Markers, Vascular Cell Markers, and Signaling Pathways in MSCs To examine the ability of long term application of mechanical loading in conditioning MSCs, the cells were treated with treatments known to cause differentiation into vascular/cardiovascular phenotypes including 5-azacitidine (5-aza), Dexamethasone with insulin (Dex+Ins), PDGF-BB, hydrocortisone (Hydrocort), EGF, VEGF-A, and TGF-β1. After seven days of loading at 0.1 Hz with 7.5% strain for 4 hours, increased polymerized actin was found after loading under control media and higher levels of polymerized actin with treatment with all of the inhibitors, except TGF-β, under static conditions (FIG. 3A). Similarly, there were increased paxillin levels for the treatments with and without load for 5-aza, Dex+Ins, EGF, and VEGF-A (FIG. 3A). Paxillin was not increased in static or loaded conditions with treatment with TGF-β1. In addition, mechanical loading increased Smad2/3 and phospho-Smad2/3 and nuclear Yap/Taz under all the treatments (FIG. 3A). The nuclear localization of Yap/Taz with mechanical loading and TGF-β treatment was markedly reduced in comparison to other treatment groups.

Figure 3B:
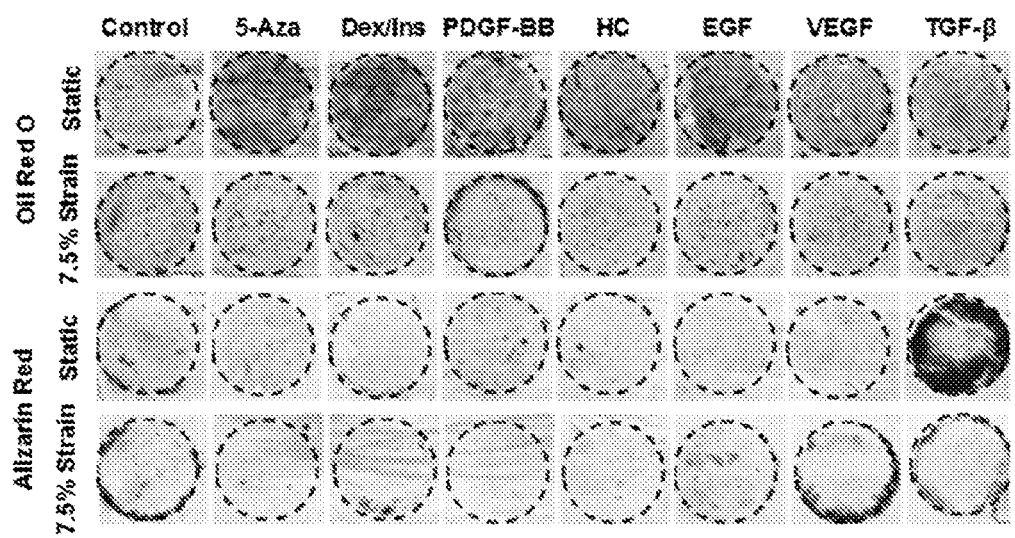

Owing to an interest in enhancing the potency of MSCs for vascular regeneration, markers of endothelial cells, vSMCs, and pluripotency-related markers were examined. Mechanical loading increased endothelial marker vWF in combination with Dex+Ins (dexamethasone and insulin) and to a lesser extent with EGF and VEGF-A (FIG. 3A). In addition, mechanical load increased PECAM-1 in combination with 5-aza and Dex+Ins (FIG. 3A). However, these treatments in most cases also led to an increase or no reduction in markers for vSMCs, including Myosin IIb and αSMA (FIG. 3A). Oct4 is a marker associated with maintenance of pluripotency in MSCs through induction of Dnmt1 expression, subsequent suppression of p16 and p21 genes and promotion of proliferation of undifferentiated phenotypes (Tsai & Hung, 2012). Under the various treatments with static conditions there was a reduction in Oct4 expression (FIG. 3A). However, with mechanical loading Oct4 was markedly increased for all the control and all treatments except VEGF-A and TGF-β1. Sca-1 has been used as a marker to identify stem cells in many tissues, although the exact nature of the isolated Sca-1+ cells remains controversial in terms of their stemness and pluripotency (Holmes & Stanford, 2007). Expression of Sca-1 has been linked functionally to cardiac repair both in knockout models and delivery of Sca-1+ cells (Bailey et al., 2012; Li et al., 2014). With the biochemical treatments, there was a reduction in Sca-1 expression but this was increased with cotreatment with mechanical load in all cases except with TGF-β1 treatment (FIG. 3A). To test for adipogenic and osteogenic differentiation, the cells were also stained using Oil Red O or Alizarin Red dye. Under static conditions there was no adipogenesis under any of the treatments with only minimal staining for several of the treatments (FIG. 3B). Osteogenesis was observed with TGF-β1 treatment under static conditions but did not occur under TGF-β1 treatment with mechanical loading (FIG. 3B).

Figure 4B:
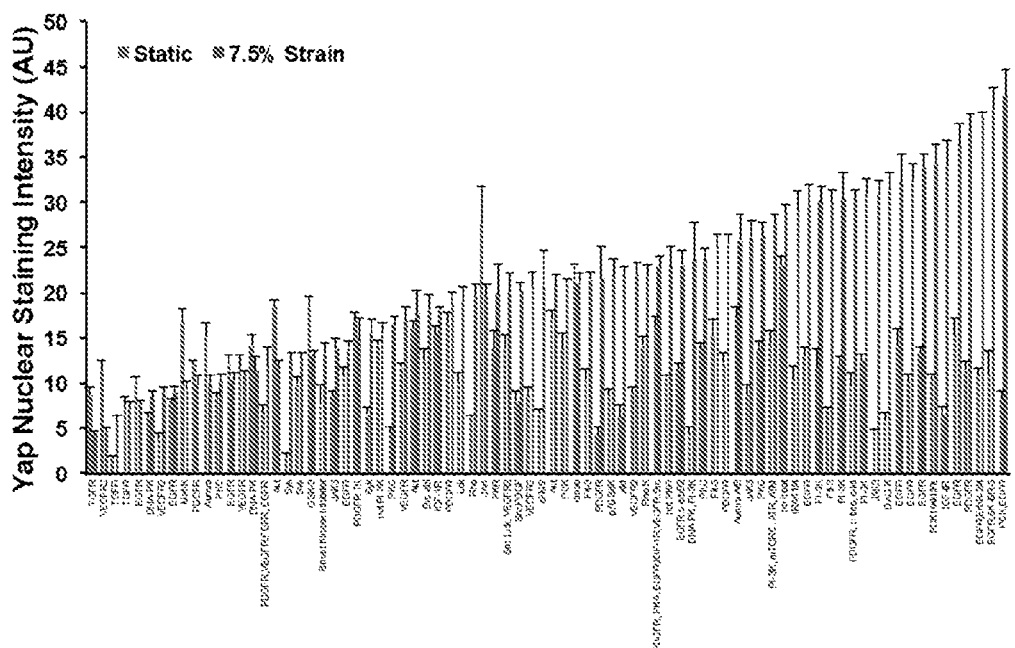
Figure 4C:
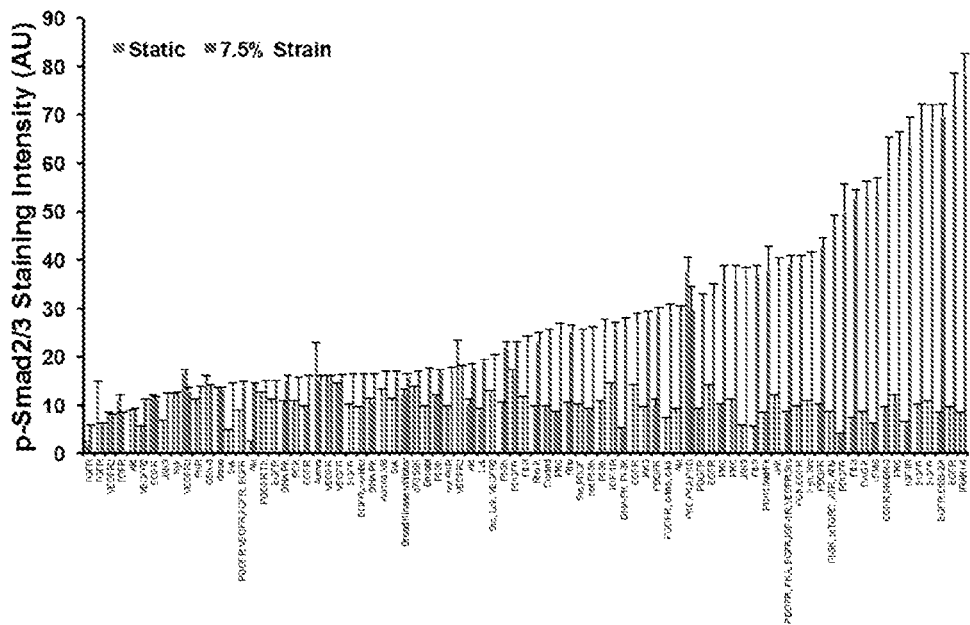
Figure 4D:
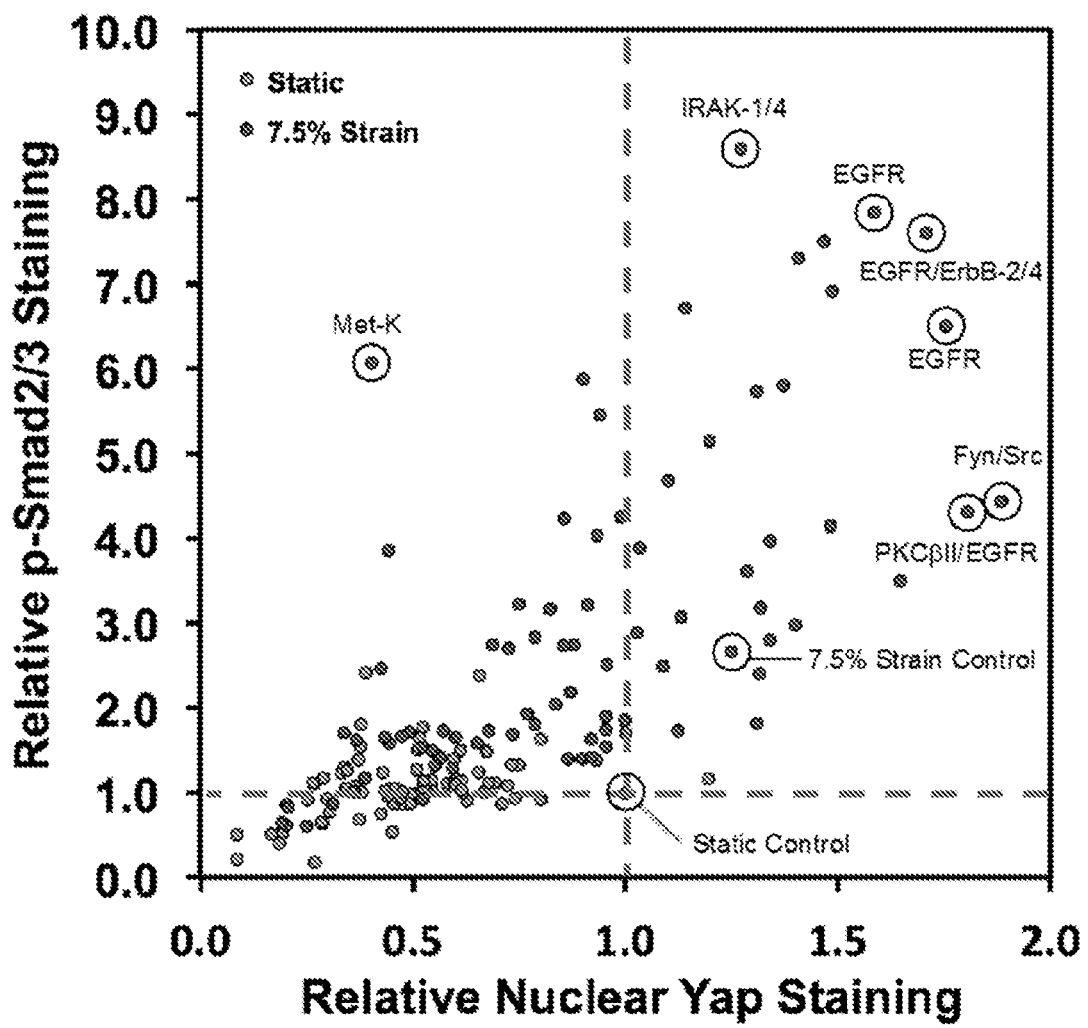

Example 5—High Throughput Drug Screening Assay with Mechanical Load Identifies Kinase Inhibitors that Enhance Smad2/3 Signaling and Hippo Pathway Activation in Synergy with Mechanical Load The HT-BOSS system was used to perform a compound screening assay to identify compounds that could enhance Smad and Hippo pathway activation in combination with mechanical load. Mechanical loading was performed on MSCs in the 96-well format in the presence of one of 80 compounds from a kinase inhibitor library. After 24 hours, immunostainining was performed for p-Smad2/3 and Yap/Taz and then quantified the nuclear staining of both signaling intermediates (FIGS. 4B-C). From this assay, compounds were identified that markedly increased both nuclear Yap and p-Smad2/3 (FIG. 4A). Many of the top hits from the assay included inhibitors of the EGFR pathways (FIG. 4D). An EGFR/ErbB-2/4 inhibitor and a PKCβII/EGFR inhibitor were chosen for further study based on the maximal activation of both pathways or maximal activation of the Hippo pathway, respectively.

Figure 5A:
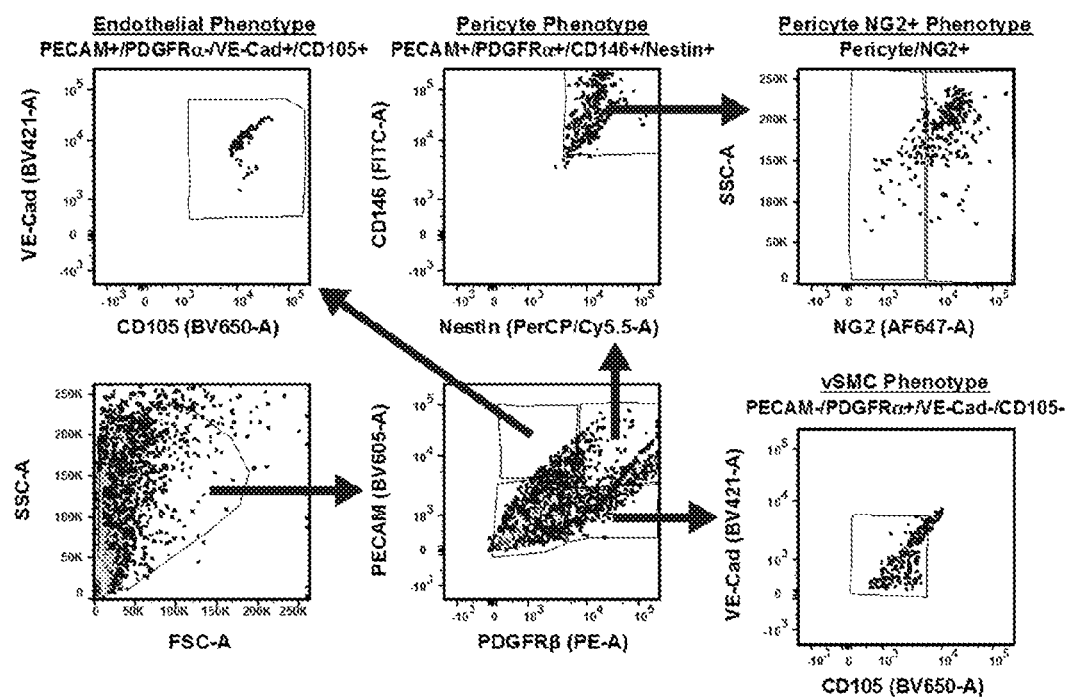
FIGS. 5A-F. Biomechanical stimulation of mesenchymal stem cells with the brachial waveform and specific small molecule inhibitors leads to a mixed phenotype expressing endothelial cell and pericyte markers with enhanced pericyte-like activity.
Figure 5B:
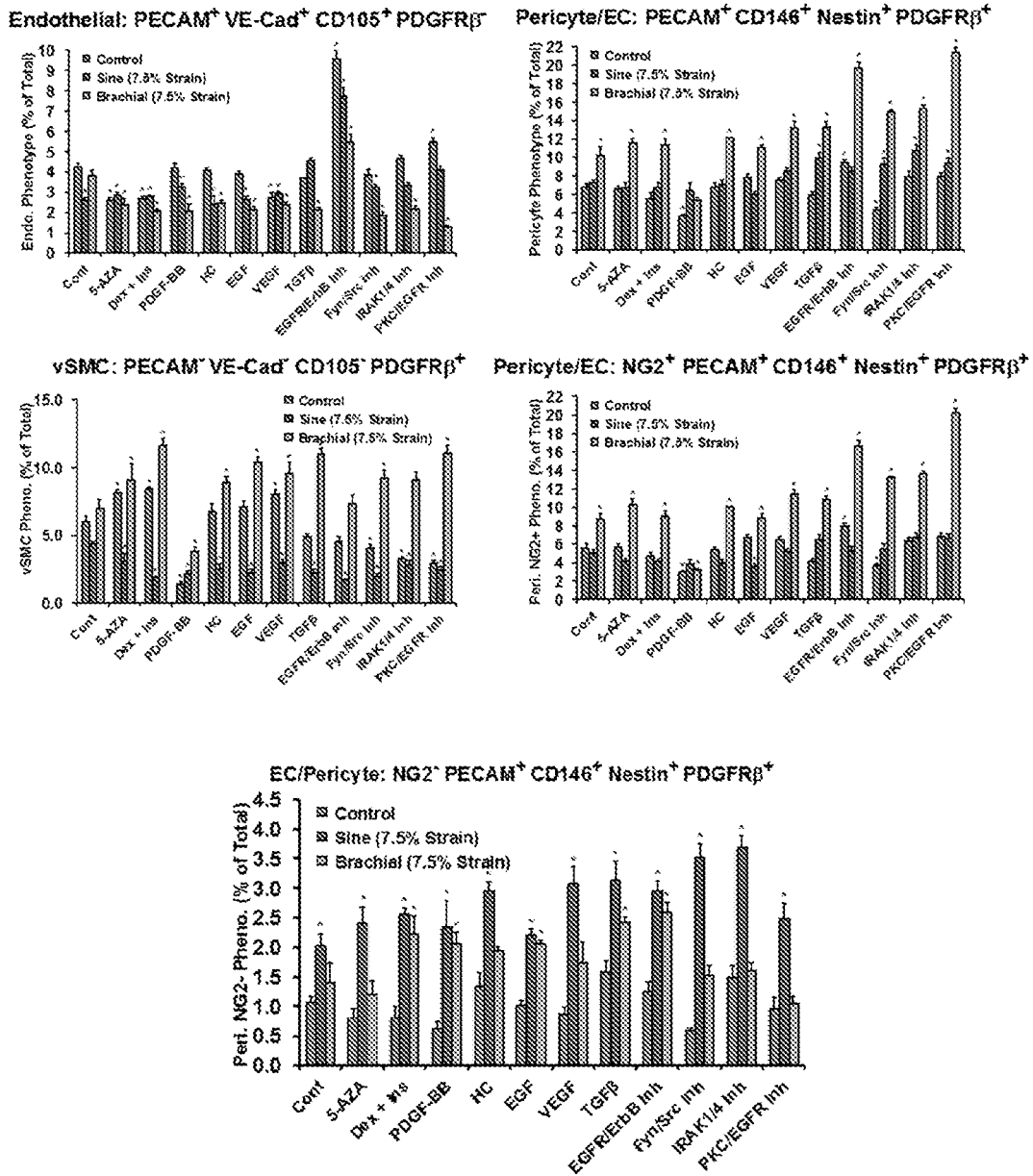

Example 6—Brachial Waveform Mechanical Loading and Pharmacological Inhibition Induce a Mixed Endothelial/Pericyte Phenotype in MSCs with Enhanced Angiogenic Properties The induction of endothelial phenotype in MSCs would be advantageous in many therapeutic applications; however, the endothelial differentiation of MSCs is controversial and there is not a consensus of which conditions produce endothelial phenotype or to what extent (Oswald et al., 2004; Laneczek Portalska et al., 2012; Galas & Liu, 2014). Recent studies have also suggested that MSCs may be derived from or identical to pericytes (Crisan et al., 2008) and pericyte markers in MSCs are correlated with enhanced regenerative properties in MSCs (Xie et al., 2015; Espagnolle et al., 2014; Russell et al., 2013; Wu et al., 2016). Moreover, many studies have been done that only look at one or two markers and conclude a phenotype of endothelial and vSMC lineage, making the true phenotype difficult to assess. To address these issues, a combinatorial set of mechanical loading and biochemical or pharmacological treatments were applied to MSCs and the phenotype assessed using multiple markers using FACS (FIG. 5A). The pharmacological inhibitors identified in the high throughput screen for compounds that synergistically activated Smad2/3 and Yap/Taz nuclear localization were included in the treatments. With this rigorous definition of endothelial phenotype there was little endothelial lineage expressed by the cells. Notably, VEGF did not increase the endothelial lineage defined by the FACS protocol. With brachial mechanical loading there was an increase in what appeared to be a mixed phenotype that had increased endothelial marker PECAM-1 and markers for pericytes including CD146, Nestin, and PDGFRβ (FIG. 5B). This population was primarily also positive for NG2, suggesting a type 2 pericyte phenotype mixed with an endothelial phenotype (FIG. 5B). Also, whether the same cells expressed other endothelial markers was checked and it was found that the vast majority expressed high levels of these as well and this phenotype was strongly unregulated by brachial loading with co-treatment with the drugs identified in the screen (i.e. PECAM$^+$CD105$^+$VECad$^+$CD146$^+$Nestin$^+$PDGFRβ$^+$NG2$^+$ cells; FIG. 5B). To analyze the true pericyte phenotype, cells that were positive for pericyte markers and negative for endothelial cells markers were measured (PECAM$^-$CD105$^-$ VECad$^-$CD146$^+$Nestin$^+$PDGFRβ$^+$ cells; FIG. 5B), which represented only a small population of the overall cells.

Figure 5C:
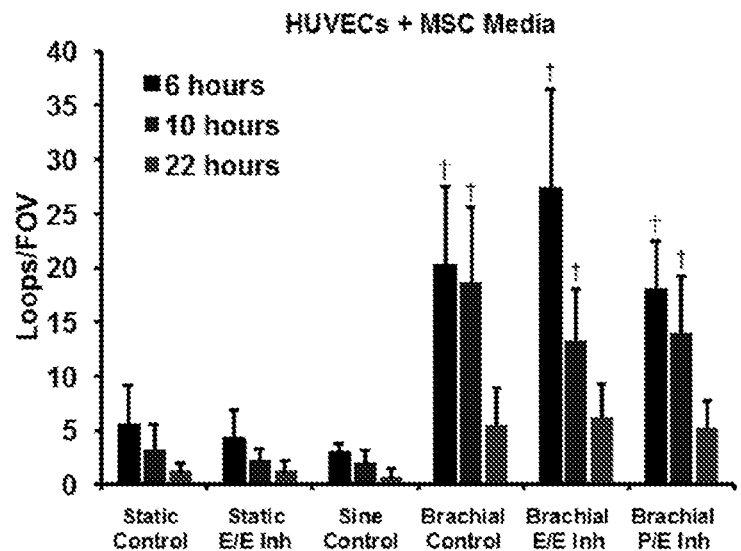
Figure 5D:
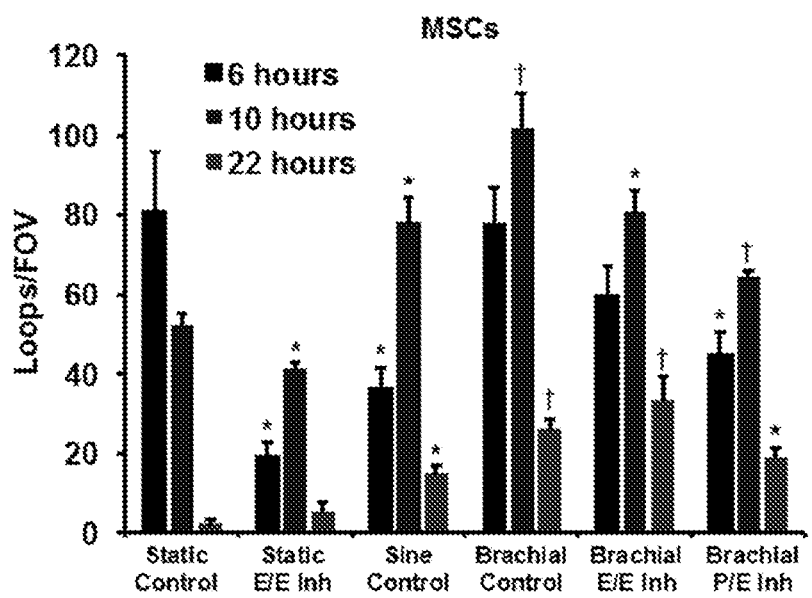
Figure 5E:
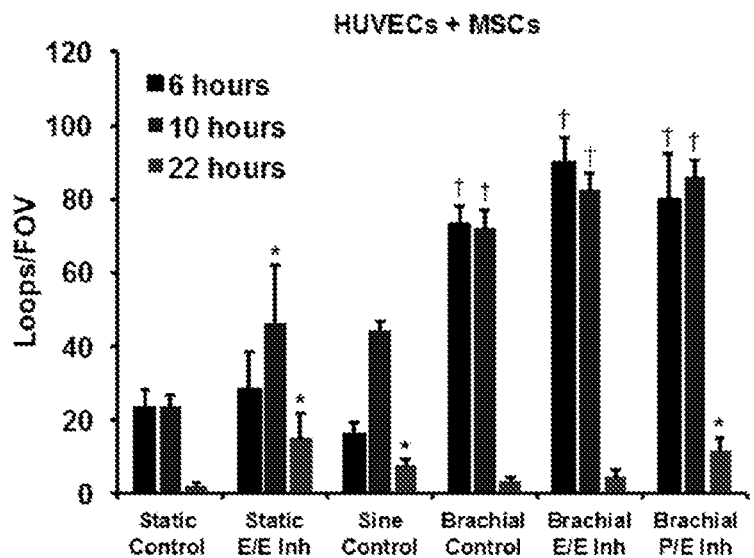

Example 7—Mechanical Conditioning into a Mixed Endothelial/Pericyte Phenotype Increases Pericyte-Like Activity and Angiogenic Properties of MSCs Whether the cells under the different conditions had increased pericyte-like behavior and proangiogenic activity was examined using a tube formation assay. The ability of MSC conditioned media to induce tube formation in endothelial cells was tested and it was found that MSC conditioned media from cells treated with brachial loading with or without pharmacological inhibitors induced increased tube formation in endothelial cells (FIG. 5C). MSCs were also plated directly on Matrigel and examined for their ability to form tubes. It was found that at the later time points there was increased stability of the tubes (FIG. 5D). MSCs were then taken and mixed with endothelial cells and plated together to examine the effect of mechanical/ biochemical conditioning on MSC pericyte-like behavior. This analysis showed that MSCs exposed to brachial waveform loading had increased tube formation in this co-culture assay (FIG. 5E).

Figure 5F:
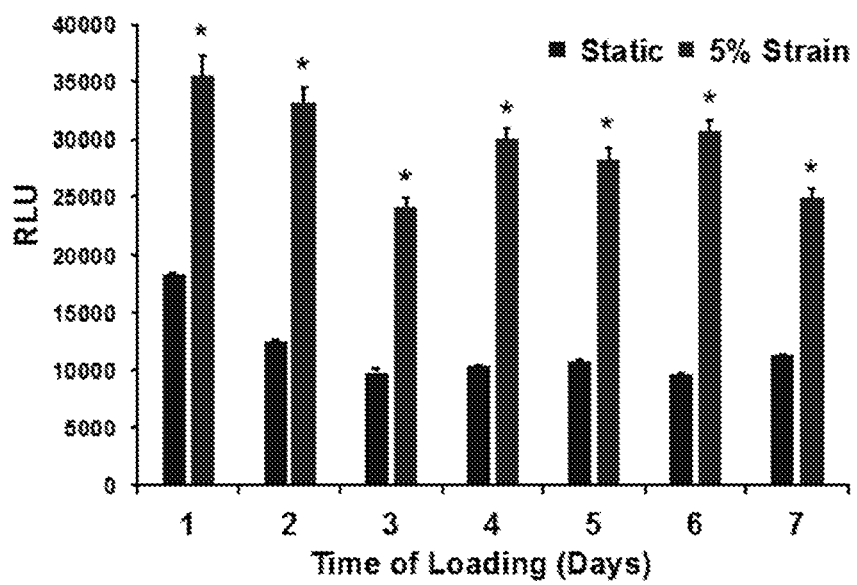
Figure 11:
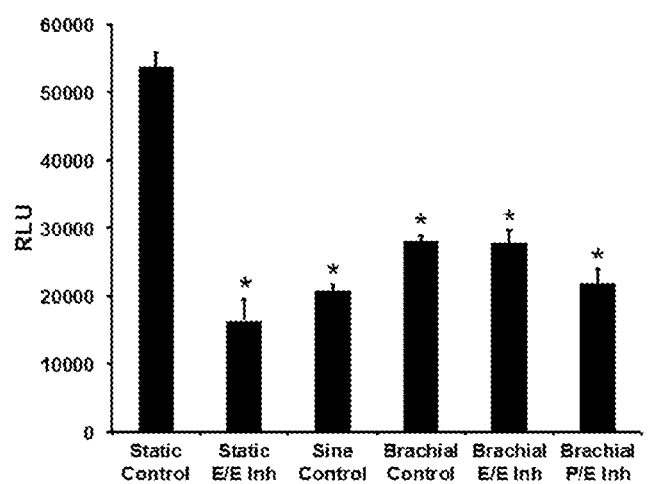
FIG. 11. Long-term loading/treatment of MSCs caused a decrease in pro-growth activity of the conditioned media towards endothelial cells as determined using an endothelial proliferation assay. Y-axis represents relative proliferation.

The mechanical conditioning was hypothesized to induce MSCs to produce increased levels of angiogenic growth factors. Mechanical loading of MSCs with the sine and brachial waveforms was performed and then the conditioned media was tested in an endothelial proliferation assay. After long-term conditioning with mechanical forces and/or pharmacological treatments, the ability of the conditioned media of the cells treated with the conditions was tested and it was found that it decreased proliferation in endothelial cells (FIG. 11). Short-term loading of MSC increased the pro-growth properties of the conditioned media on endothelial cells (FIG. 5F). Long-term loading/treatment of MSCs, however, caused a decrease in pro-growth activity of the conditioned media towards endothelial cells (FIG. 11).

Figure 9:
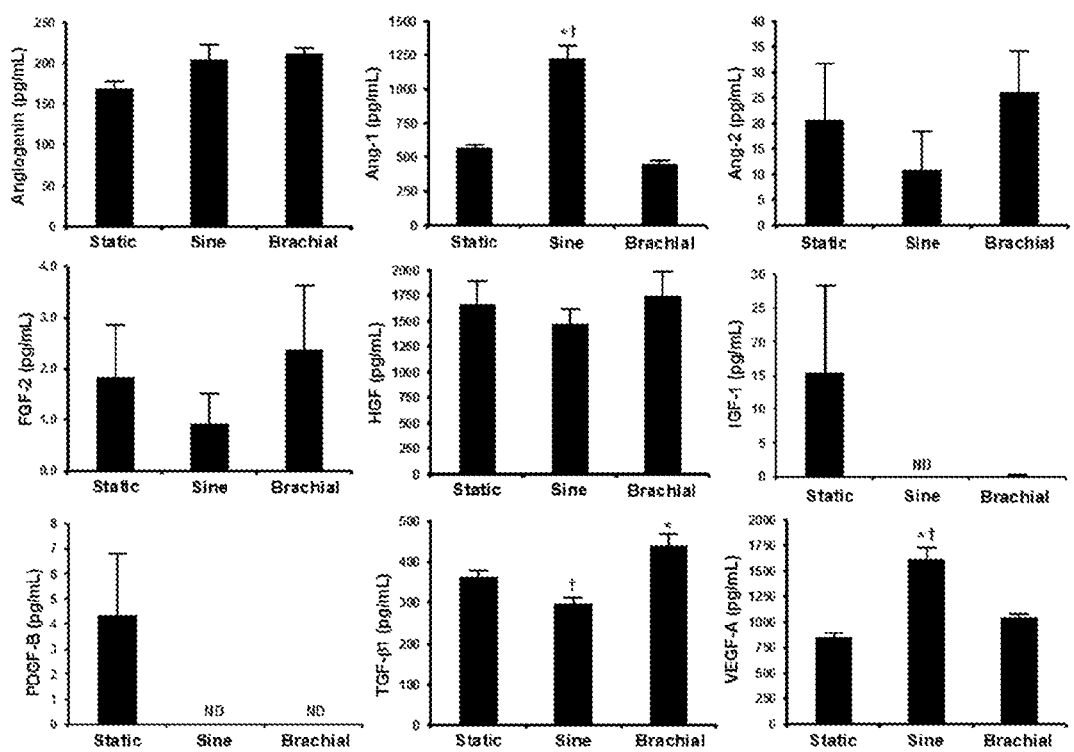
FIG. 9. Angiogenic factors in MSC conditioned media after 24 hours of the indicated treatments. The growth factors were measured using ELISA assays. *p<0.05 versus cells treated with static conditions under control treatment. †p<0.05 versus mechanically strained control group.
Figure 10:
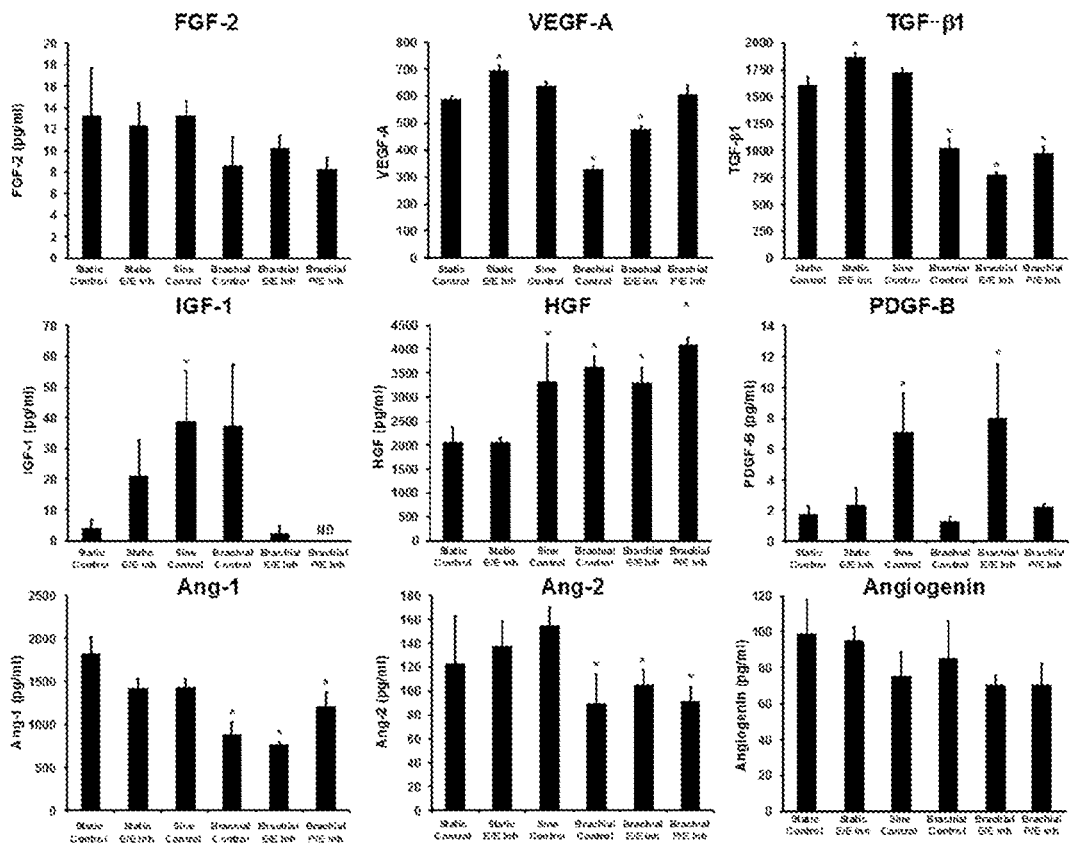
FIG. 10. Angiogenic factors in MSC conditioned media after 7 days of the indicated treatments. The growth factors were measured using ELISA assays. *p<0.05 versus cells treated with static conditions under control treatment.

The production of growth factors by MSCs was examined under mechanical loading in the short term (24 hours) and the long term (7 days) with co-treatment with pharmacological inhibitors. After short term conditioning, a significant increase in Ang-1 and VEGF-A was found with sine waveform loading as well as a significant increase in TGF-β1 with brachial loading (FIG. 9). After long term loading, a significant increase in HGF was found for all loaded conditions. In addition, increased PDGF-B was found in sine and brachial loading with ErbB/EGFR inhibitor treatment (FIG. 10).

Figure 6A:
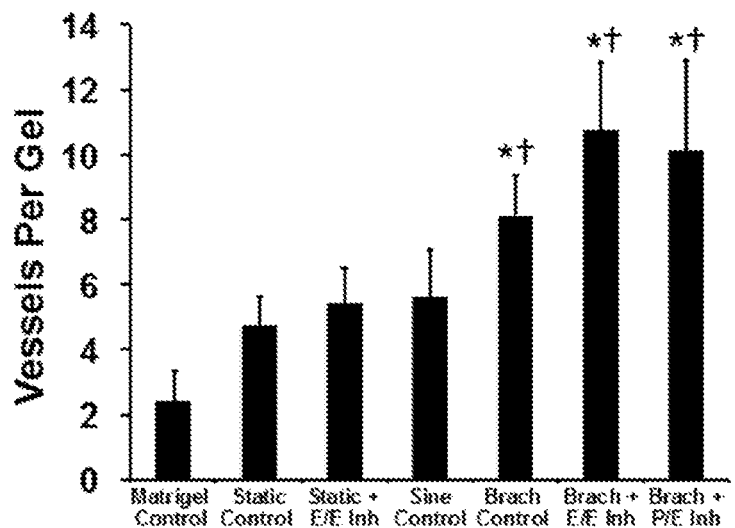
FIGS. 6A-D. Analysis of the effects of mechanical loading and pharmacological conditioning on the in vivo angiogenic properties of MSCs.
Figure 6B:
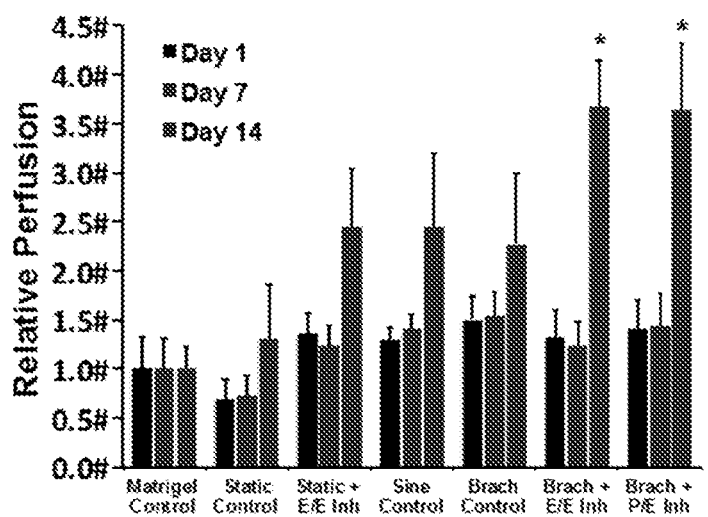
Figure 6C:
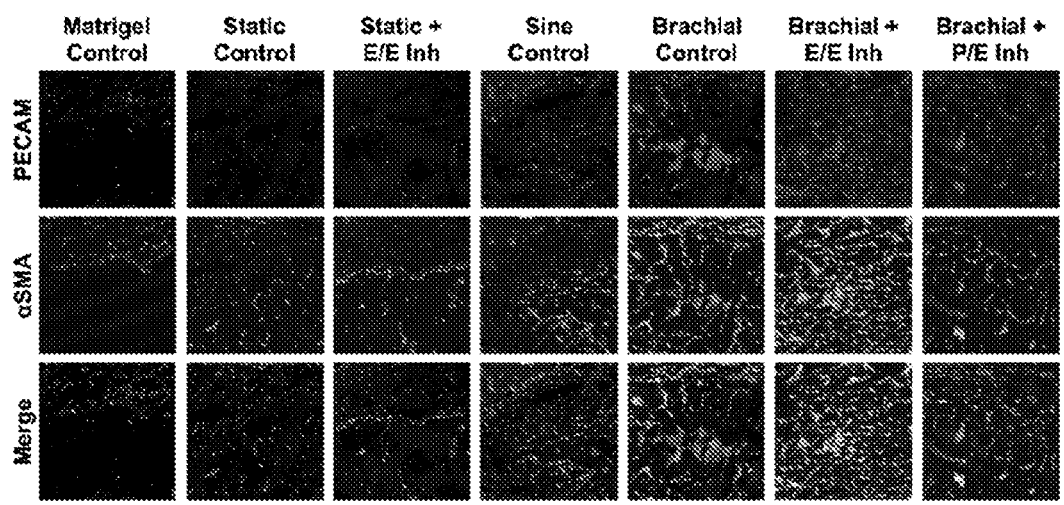
Figure 6D:
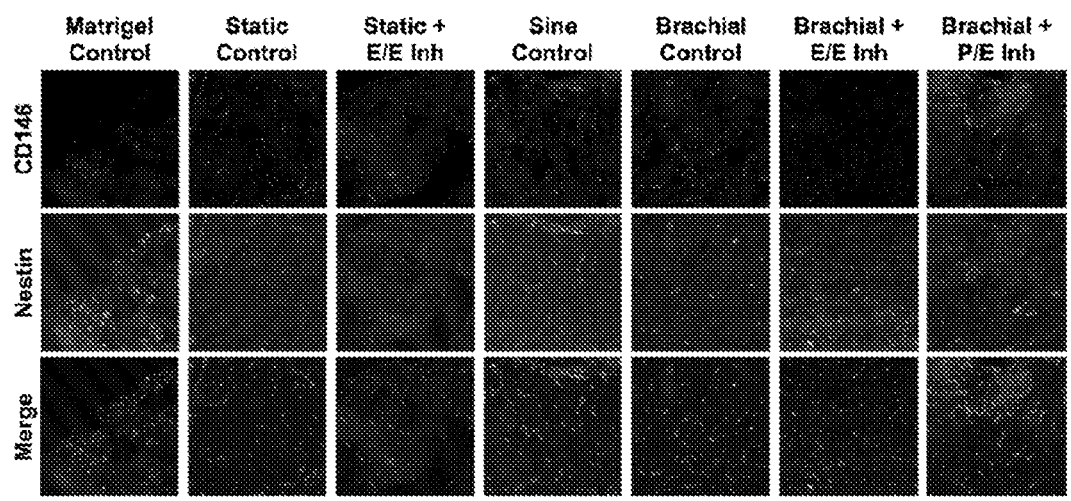

Example 8—Optimal Mechanical and Pharmacological Conditioning of MSCs Increases Proangiogenic Potential Following Implantation The effects of mechanical loading and pharmacological conditioning on the in vivo angiogenic properties of MSCs was examined. The cells were conditioned with the various treatments for 7 days and then implanted them subcutaneously in nu/nu mice in Matrigel. After 14 days, there were increased numbers of vessels invading the gels implanted with MSCs exposed to brachial waveform mechanical loading based on macroscopic images of the implant (FIG. 6A). In particular, the cells treated with the brachial waveform loading and pharmacological co-treatment had the highest levels of large vessels invading. Analysis with laser speckle imaging revealed increased perfusion on the flanks of brachial waveform loaded MSCs with pharmacological co-treatment, consistent with the macroscopic appearance of the implants (FIG. 6B). Histological analysis of the gels also supported these findings and demonstrated increased levels of PECAM with mechanical loading and mechanical loading in combination with pharmacological co-treatment (FIGS. 6C-D).

Example 9—In Vivo Testing of Conditioned Human MSCs

Conditioned human MSCs were subcutaneously implanted into a mouse model. Fluorescence in situ hybridization was used to label the X chromosome of the human cells in histological sections from the tissue. Human cells remained alive in the mice after 14 days of implantation.

The efficacy of conditioned hMSCs in treating ischemia was examined by implanting the cells in a model of hindlimb ischemia in immune compromised mice. Following conditioning, the cells were detached from the loading plate using 0.05% Trypsin-EDTA. The cells were resuspended in alginate beads 2% RGD peptides and 0.045% collagen. The femoral artery was ligated in the mice to create ischemia in one limb. The alginate suspended cells were implanted into the ischemic leg for 14 days.

Figure 12:
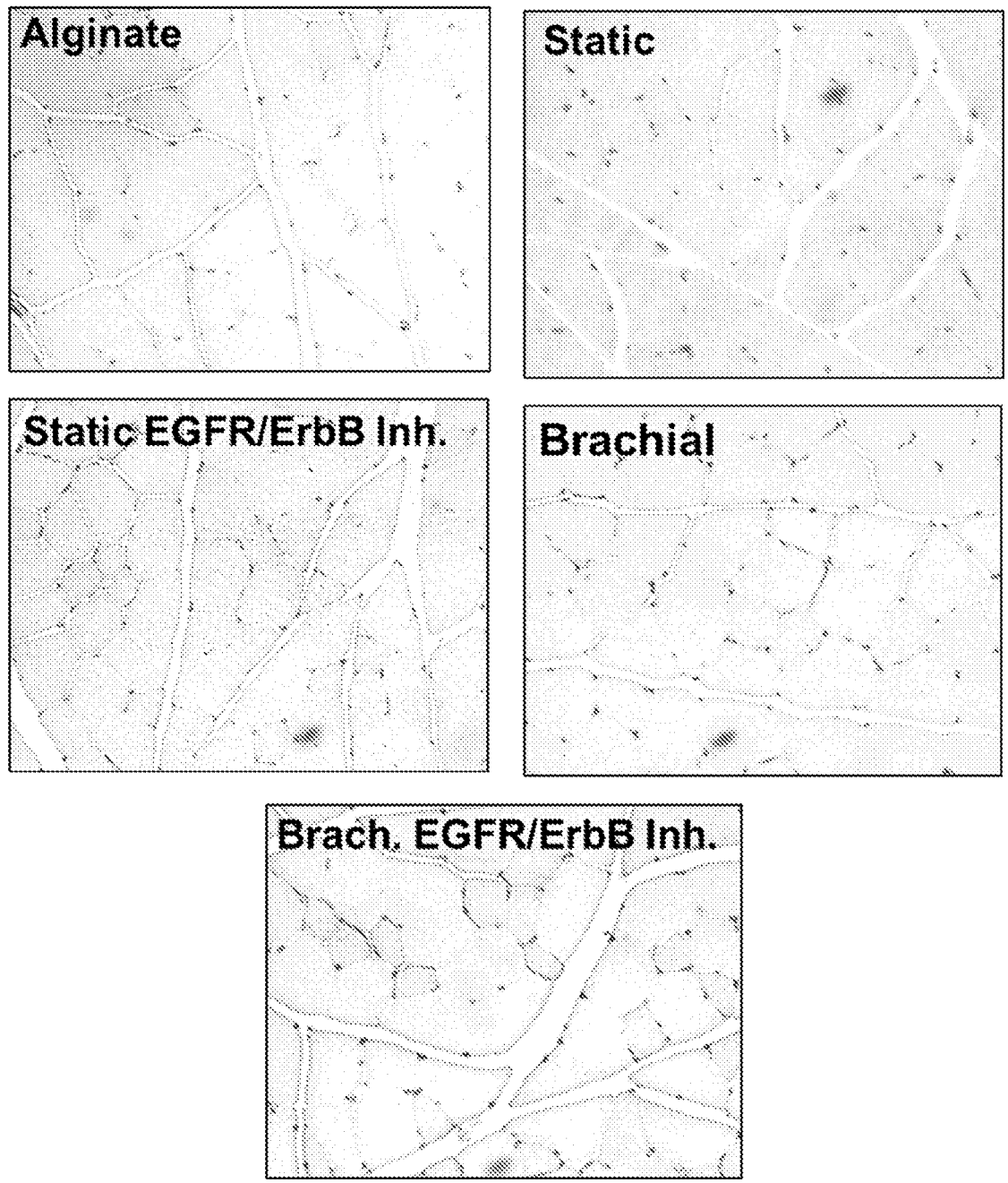
FIG. 12. Histological sections immunostained for PECAM (blood vessels) from the calves of hind limb ischemia model mice into which human conditioned MSCs had been implanted.
Figure 13:
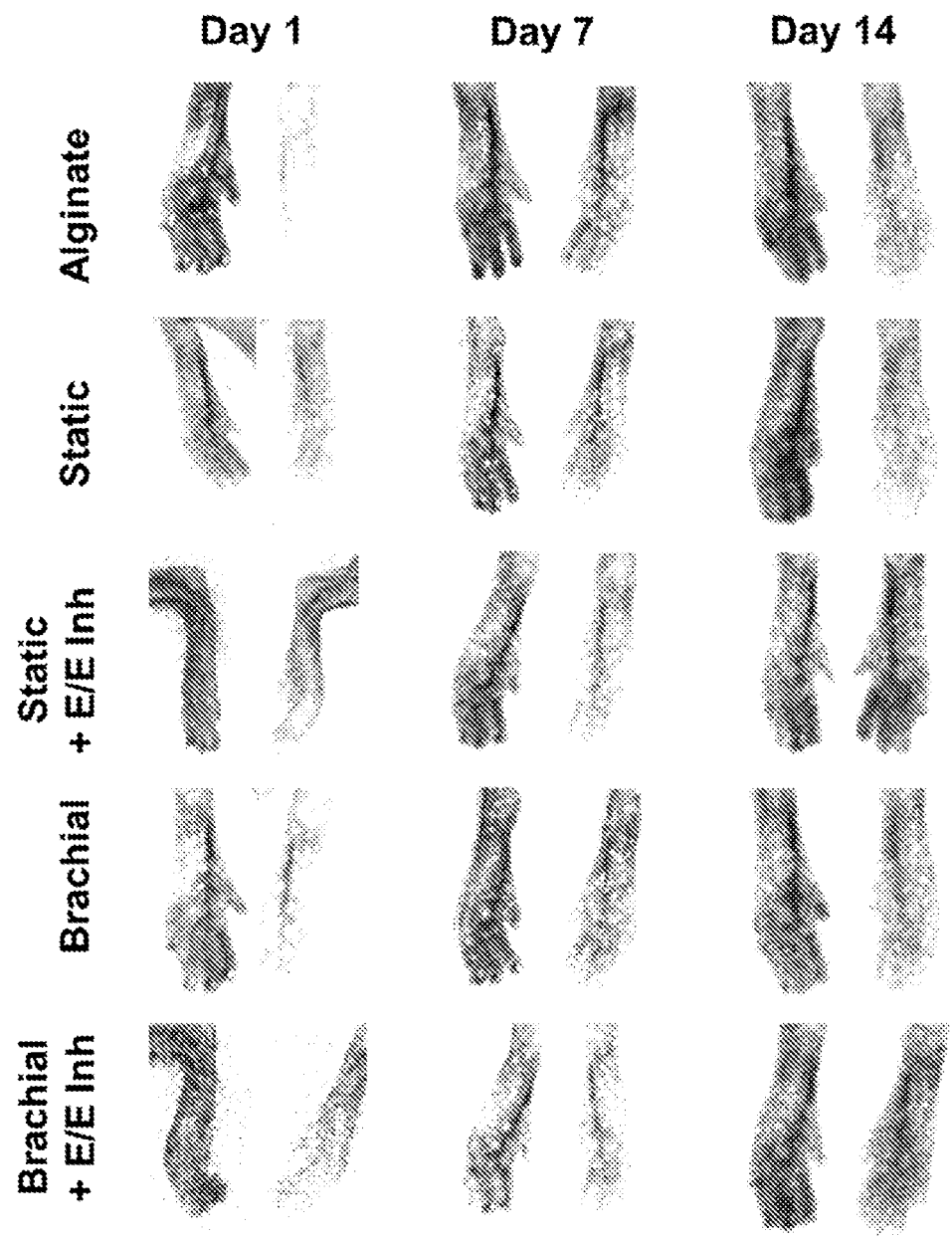
FIG. 13. Laser speckle imaging of blood flow through the hind limbs of ischemic mice. Darker signal in the limb indicates higher blood flow. Light or no signal indicates reduced or no blood flow in the limb.

Histological sections of tissue from the calf of the animals, immunostained for PECAM (blood vessels), are shown in FIG. 12. Increased blood vessels were seen in tissues treated with MSCs conditioned with brachial waveform mechanical loading and brachial waveform mechanical loading with EGFR/ErbB inhibitor treated cells. In addition, blood flow through the limbs of the mice was assessed using a custom laser speckle imaging system (FIG. 13). Decreased ratio of the signal between the ischemic (ISCH) and control (CRTL) limb is indicative of recovery from ischemia. Darker signal in the limb indicates higher blood flow and light or no signal indicates reduced or no blood flow that is characteristic of ischemic legs. By day 14, the static cells+ EGFR/ErbB inhibitor, brachial waveform and brachial waveform+EGFR/ErbB inhibitor treated cells showed improved recovery over mice treated with alginate or static cultured cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ai, W. J., et al. R-Smad signaling-mediated VEGF expression coordinately regulates endothelial cell differentiation of rat mesenchymal stem cells. *Stem Cells Dev* 24, 1320-1331 (2015).

Alaminos, M., et al. Transdifferentiation potentiality of human Wharton's jelly stem cells towards vascular endothelial cells. *J Cell Physiol* 223, 640-647 (2010).

Armulik, A., Genove, G. & Betsholtz, C. Pericytes: developmental, physiological, and pathological perspectives, problems, and promises. *Dev Cell* 21, 193-215 (2011).

Bai, K., Huang, Y., Jia, X., Fan, Y. & Wang, W. Endothelium oriented differentiation of bone marrow mesenchymal stem cells under chemical and mechanical stimulations. *J Biomech* 43, 1176-1181 (2010).

Bailey, B., et al. Sca-1 knockout impairs myocardial and cardiac progenitor cell function. *Circ Res* 111, 750-760 (2012).

Baraniak, P. R. & McDevitt, T. C. Stem cell paracrine actions and tissue regeneration. *Regen Med* 5, 121-143 (2010).

Barbash, I. M., et al. Systemic delivery of bone marrow-derived mesenchymal stem cells to the infarcted myocardium: feasibility, cell migration, and body distribution. *Circulation* 108, 863-868 (2003).

Barkholt, L., et al. Risk of tumorigenicity in mesenchymal stromal cell-based therapies—bridging scientific observations and regulatory viewpoints. *Cytotherapy* 15, 753-759 (2013).

Birbrair, A., et al. Role of pericytes in skeletal muscle regeneration and fat accumulation. *Stem Cells Dev* 22, 2298-2314 (2013).

Birbrair, A., et al. Type-2 pericytes participate in normal and tumoral angiogenesis. *Am J Physiol Cell Physiol* 307, C25-38 (2014).

Brown, T. D. Techniques for mechanical stimulation of cells in vitro: a review. *J Biomech* 33, 3-14 (2000).

Bussolino, F., et al. Hepatocyte growth factor is a potent angiogenic factor which stimulates endothelial cell motility and growth. *J Cell Biol* 119, 629-641 (1992).

Cai, M., et al. PET monitoring angiogenesis of infarcted myocardium after treatment with vascular endothelial growth factor and bone marrow mesenchymal stem cells. *Amino Acids* 48, 811-820 (2016a).

Cai, M., et al. Bone Marrow Mesenchymal Stem Cells (BM-MSCs) Improve Heart Function in Swine Myocardial Infarction Model through Paracrine Effects. *Sci Rep* 6, 28250 (2016b).

Cassino, T. R., et al. Mechanical loading of stem cells for improvement of transplantation outcome in a model of acute myocardial infarction: the role of loading history. *Tissue Eng Part A* 18, 1101-1108 (2012).

Crisan, M., et al. A perivascular origin for mesenchymal stem cells in multiple human organs. *Cell Stem Cell* 3, 301-313 (2008).

Di Bernardini, E., et al. Endothelial lineage differentiation from induced pluripotent stem cells is regulated by microRNA-21 and transforming growth factor beta2 (TGF-beta2) pathways. *J Biol Chem* 289, 3383-3393 (2014).

Dong, J. D., et al. Response of mesenchymal stem cells to shear stress in tissue-engineered vascular grafts. *Acta Pharmacol Sin* 30, 530-536 (2009).

Du, W. J., et al. Heterogeneity of proangiogenic features in mesenchymal stem cells derived from bone marrow, adipose tissue, umbilical cord, and placenta. Stem Cell Res Ther 7, 163 (2016).

Engler, A. J., Sen, S., Sweeney, H. L. & Discher, D. E. Matrix elasticity directs stem cell lineage specification. *Cell* 126, 677-689 (2006).

Espagnolle, N., et al. CD146 expression on mesenchymal stem cells is associated with their vascular smooth muscle commitment. *J Cell Mol Med* 18, 104-114 (2014).

Galas, R. J., Jr. & Liu, J. C. Vascular endothelial growth factor does not accelerate endothelial differentiation of human mesenchymal stem cells. *J Cell Physiol* 229, 90-96 (2014).

Goldie, L. C., Nix, M. K. & Hirschi, K. K. Embryonic vasculogenesis and hematopoietic specification. *Organogenesis* 4, 257-263 (2008).

Heeschen, C., et al. Profoundly reduced neovascularization capacity of bone marrow mononuclear cells derived from patients with chronic ischemic heart disease. *Circulation* 109, 1615-1622 (2004).

Heldin, C. H., Rubin, K., Pietras, K. & Ostman, A. High interstitial fluid pressure—an obstacle in cancer therapy. *Nat Rev Cancer* 4, 806-813 (2004).

Henderson, K., Sligar, A. D., Le, V., Lee, J. & Baker, A. B. Biomechanical Regulation of Mesenchymal Stem Cells for Cardiovascular Tissue Engineering. *Advanced Healthcare Materials* (2017).

Hill, J. M., et al. Circulating endothelial progenitor cells, vascular function, and cardiovascular risk. *N Engl J Med* 348, 593-600 (2003).

Holmes, C. & Stanford, W. L. Concise review: stem cell antigen-1: expression, function, and enigma. *Stem Cells* 25, 1339-1347 (2007).

Homayouni Moghadam, F., et al. Treatment with platelet lysate induces endothelial differentiation of bone marrow mesenchymal stem cells under fluid shear stress. *EXCLI J* 13, 638-649 (2014).

Jain, R. K., Martin, J. D. & Stylianopoulos, T. The role of mechanical forces in tumor growth and therapy. *Annu Rev Biomed Eng* 16, 321-346 (2014).

Janeczek Portalska, K., et al. Endothelial differentiation of mesenchymal stromal cells. *PLoS One* 7, e46842 (2012).

Kamotani, Y., et al. Individually programmable cell stretching microwell arrays actuated by a Braille display. *Biomaterials* 29, 2646-2655 (2008).

Kim, D. H., et al. Shear stress and circumferential stretch by pulsatile flow direct vascular endothelial lineage commitment of mesenchymal stem cells in engineered blood vessels. *J Mater Sci Mater Med* 27, 60 (2016).

Kinnaird, T., et al. Local delivery of marrow-derived stromal cells augments collateral perfusion through paracrine mechanisms. *Circulation* 109, 1543-1549 (2004).

Korn, J., Christ, B. & Kurz, H. Neuroectodermal origin of brain pericytes and vascular smooth muscle cells. *J Comp Neurol* 442, 78-88 (2002).

Kretlow, J. D., et al. Donor age and cell passage affects differentiation potential of murine bone marrow-derived stem cells. *BMC Cell Biol* 9, 60 (2008).

Lee, D. A., Knight, M. M., Campbell, J. J. & Bader, D. L. Stem cell mechanobiology. *J Cell Biochem* 112, 1-9 (2011).

Lee, J., Wong, M., Smith, Q. & Baker, A. B. A novel system for studying mechanical strain waveform-dependent responses in vascular smooth muscle cells. *Lab Chip* 13, 4573-4582 (2013).

Lee, J. & Baker, A. B. Computational analysis of fluid flow within a device for applying biaxial strain to cultured cells. *J Biomech Eng* 137, 051006 (2015).

Li, T. S., et al. Impaired potency of bone marrow mononuclear cells for inducing therapeutic angiogenesis in obese diabetic rats. *Am J Physiol Heart Circ Physiol* 290, H1362-1369 (2006).

Li, Q., et al. VEGF treatment promotes bone marrow-derived CXCR4+ mesenchymal stromal stem cell differentiation into vessel endothelial cells. *Exp Ther Med* 13, 449-454 (2017).

Li, N., Pasha, Z. & Ashraf, M. Reversal of ischemic cardiomyopathy with Sca-1+ stem cells modified with multiple growth factors. *PLoS One* 9, e93645 (2014).

MacQueen, L., Sun, Y. & Simmons, C. A. Mesenchymal stem cell mechanobiology and emerging experimental platforms. *J R Soc Interface* 10, 20130179 (2013).

Muller-Ehmsen, J., et al. Effective engraftment but poor mid-term persistence of mononuclear and mesenchymal bone marrow cells in acute and chronic rat myocardial infarction. *J Mol Cell Cardiol* 41, 876-884 (2006).

Nagaya, N., et al. Intravenous administration of mesenchymal stem cells improves cardiac function in rats with acute myocardial infarction through angiogenesis and myogenesis. *Am J Physiol Heart Circ Physiol* 287, H2670-2676 (2004).

Oswald, J., et al. Mesenchymal stem cells can be differentiated into endothelial cells in vitro. *Stem Cells* 22, 377-384 (2004).

Phinney, D. G. Functional heterogeneity of mesenchymal stem cells: implications for cell therapy. *J Cell Biochem* 113, 2806-2812 (2012).

Roobrouck, V. D., Ulloa-Montoya, F. & Verfaillie, C. M. Self-renewal and differentiation capacity of young and aged stem cells. *Exp Cell Res* 314, 1937-1944 (2008).

Russell, K. C., et al. Cell-surface expression of neuron-glial antigen 2 (NG2) and melanoma cell adhesion molecule (CD146) in heterogeneous cultures of marrow-derived mesenchymal stem cells. *Tissue Eng Part A* 19, 2253-2266 (2013).

Shake, J. G., et al. Mesenchymal stem cell implantation in a swine myocardial infarct model: engraftment and functional effects. *Ann Thorac Surg* 73, 1919-1925; discussion 1926 (2002).

Shi, Y., et al. Mesenchymal stem cells: a new strategy for immunosuppression and tissue repair. *Cell Res* 20, 510-518 (2010).

Simmons, C. S., et al. Integrated strain array for cellular mechanobiology studies. *J Micromech Microeng* 21, 54016-54025 (2011).

Spencer, A., et al. A high-throughput mechanofluidic screening platform for investigating tumor cell adhesion during metastasis. *Lab Chip* 16, 142-152 (2015).

Spruell, C. & Baker, A. B. Analysis of a high-throughput cone-and-plate apparatus for the application of defined spatiotemporal flow to cultured cells. *Biotechnol Bioeng* 110, 1782-1793 (2013).

Tamama, K., Sen, C. K. & Wells, A. Differentiation of bone marrow mesenchymal stem cells into the smooth muscle lineage by blocking ERK/MAPK signaling pathway. *Stem Cells Dev* 17, 897-908 (2008).

Tsai, C. C. & Hung, S. C. Functional roles of pluripotency transcription factors in mesenchymal stem cells. *Cell Cycle* 11, 3711-3712 (2012).

Voyvodic, P. L., Min, D. & Baker, A. B. A multichannel dampened flow system for studies on shear stress-mediated mechanotransduction. *Lab Chip* 12, 3322-3330 (2012).

Wagner, W., et al. Aging and replicative senescence have related effects on human stem and progenitor cells. *PLoS One* 4, e5846 (2009).

Wang, H., et al. Shear stress induces endothelial differentiation from a murine embryonic mesenchymal progenitor cell line. *Arterioscler Thromb Vasc Biol* 25, 1817-1823 (2005).

Watt, S. M., et al. The angiogenic properties of mesenchymal stem/stromal cells and their therapeutic potential. *Br Med Bull* 108, 25-53 (2013).

Wu, C. C., Liu, F. L., Sytwu, H. K., Tsai, C. Y. & Chang, D. M. CD146+ mesenchymal stem cells display greater therapeutic potential than CD146− cells for treating collagen-induced arthritis in mice. *Stem Cell Res Ther* 7, 23 (2016).

Xie, L., Zeng, X., Hu, J. & Chen, Q. Characterization of Nestin, a Selective Marker for Bone Marrow Derived Mesenchymal Stem Cells. *Stem Cells Int* 2015, 762098 (2015).

Yan, J., Tie, G., Xu, T. Y., Cecchini, K. & Messina, L. M. Mesenchymal stem cells as a treatment for peripheral arterial disease: current status and potential impact of type II diabetes on their therapeutic efficacy. *Stem Cell Rev* 9, 360-372 (2013).

Yang, M. T., Fu, J., Wang, Y. K., Desai, R. A. & Chen, C. S. Assaying stem cell mechanobiology on microfabricated elastomeric substrates with geometrically modulated rigidity. *Nat Protoc* 6, 187-213 (2011).

What is claimed is:

1. A mesenchymal stem cell-derived cell comprising both an endothelial phenotype, characterized by the expression of PECAM-1, CD105, and VECad, and a pericyte phenotype, characterized by the expression of CD146, Nestin, and PDGFRβ, wherein the cell expresses PECAM-1, CD105, VECad, CD146, Nestin, and PDGFRβ.

2. The cell of claim 1, wherein the pericyte phenotype is a type 2 pericyte phenotype further characterized by the expression of NG2.

3. The cell of claim 1, wherein the cell further expresses NG2.

4. The cell of claim 1, wherein the cell is not genetically modified.

5. The cell of claim 1, wherein the cell has increased YAP/TAZ activation and increased SMAD2/3 activation.

6. A composition of cells having a combined pericyte/endothelial phenotype produced by a method comprising:
   (a) obtaining a starting population of mesenchymal stem cells;
   (b) culturing the mesenchymalstem cells on a flexible surface that allows cell adhesion;
   (c) applying a controlled mechanical stretch using a brachial waveform having a frequency of 0.1 Hz-1.00 Hz and a magnitude of strain of 0.1% to 17.5% to the mesenchymal stem cells with a force sufficient to produce a conditioned composition comprising cells having a combined pericyte/endothelial phenotype; and
   (d) incubating the mesenchymal stem cells with at least one pharmacological agent that inhibits EGFR signaling,
wherein the cells having a combined pericyte/endothelial phenotype expresses an increased level of PECAM-1, CD105, VECad, CD146, Nestin, and PDGFRB as compared to the starting VECad indicate the pericyte phenotype, and the increased level of CD146 population of mesenchymal stem cells, wherein the increased level of PECAM-1, CD105, and VECad indicate the pericyte phenotype, and the increased level of CD146, Nestin, and PDGFRβ indicate the endothelial phenotype.

7. The composition of claim 6, wherein the pericyte phenotype is a type 2 pericyte phenotype.

8. The composition of claim 6, wherein the brachial waveform has a magnitude of 7.5% strain and a frequency of 0.1 Hz.

9. The composition of claim 6, wherein the at least one pharmacological agent that inhibits EGFR signaling is an EGFR/Erb-2/4 kinase inhibitor or a PKCβII/EGFR kinase inhibitor.

10. A composition comprising a therapeutically effective amount of cells having a combined pericyte/endothelial phenotype produced by a method comprising:
    (a) obtaining from a patient a first starting population of mesenchymal stem cells (MSCs);
    (b) preparing multiple, separate cultures of the first starting population of MSCs on flexible surfaces that allow cell adhesion;
    (c) applying a variety of brachial waveforms having a frequency of 0.1 Hz-1.00 Hz and a magnitude of strain of 0.1% to 17.5% and at least one pharmacological agent that inhibits EGFR signaling to each of the cultures;
    (d) screening the cultured cells for markers of a combined pericyte/endothelial cell phenotype, thereby identifying conditions for enhancing MSC therapies for the patient;
    (e) obtaining from the patient a second starting population of mesenchymal stem cells (MSCs);
    (f) culturing the second starting population of MSCs on a flexible surface that allows cell adhesion; and
    (g) applying the conditions identified following step (d) to the second starting population of MSCs on the flexible surface that allows cell adhesion, thereby producing a therapeutically effective amount of cells having a combined pericyte/endothelial phenotype,
    wherein the cells having a combined pericyte/endothelial phenotype expresses an increased level of PECAM-1, CD105, VECad, CD146, Nestin, and PDGFRβ as compared to the first or second starting population of mesenchymal stem cells, wherein the increased level of PECAM-1, CD105, and VECad indicate the pericyte phenotype, and the increased level of CD146, Nestin, and PDGFRβ indicate the endothelial phenotype.

11. The composition of claim 10, wherein the markers of a combined pericyte/endothelial cell phenotype comprise nuclear localization of YAP/TAZ, phosphorylation of SMAD2/3, nuclear localization of SMAD2/3, and increased expression of PECAM-1.

12. The composition of claim 10, wherein the at least one pharmacological agent that inhibits EGFR signaling is an EGFR/Erb-2/4 kinase inhibitor or a PKCβII/EGFR kinase inhibitor.

* * * * *

UNITED STATES PATENT AND TRADEMARK OFFICE
CERTIFICATE OF CORRECTION

PATENT NO. : 12,064,453 B2  
APPLICATION NO. : 16/650195  
DATED : August 20, 2024  
INVENTOR(S) : Aaron B. Baker and Jason Lee Page 1 of 1

It is certified that error appears in the above-identified patent and that said Letters Patent is hereby corrected as shown below:

In the Claims

In Claim 6, Column 28, Line 64, delete "PDGFRB" and insert -- PDGFRβ -- therefor.

Signed and Sealed this  
Twenty-sixth Day of November, 2024

Katherine Kelly Vidal  
*Director of the United States Patent and Trademark Office*